United States Patent
Cook et al.

(10) Patent No.: US 8,258,301 B2
(45) Date of Patent: Sep. 4, 2012

(54) UROTENSIN II RECEPTOR ANTAGONISTS

(75) Inventors: Brian Nicholas Cook, Danbury, CT (US); Anne Bettina Eldrup, Danbury, CT (US); Ingo Andreas Mugge, New Haven, CT (US); Fariba Soleymanzadeh, Danbury, CT (US); Sanxing Sun, Danbury, CT (US); Yunlong Zhang, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 327 days.

(21) Appl. No.: 12/527,973

(22) PCT Filed: May 12, 2008

(86) PCT No.: PCT/US2008/063370
§ 371 (c)(1), (2), (4) Date: Sep. 24, 2009

(87) PCT Pub. No.: WO2008/144268
PCT Pub. Date: Nov. 27, 2008

(65) Prior Publication Data
US 2010/0121051 A1  May 13, 2010

Related U.S. Application Data

(60) Provisional application No. 60/930,283, filed on May 15, 2007.

(51) Int. Cl.
C07D 471/04 (2006.01)
(52) U.S. Cl. ........ 546/122; 544/362; 544/127; 544/316; 544/331; 540/597
(58) Field of Classification Search .......... 546/122; 544/362, 127, 316, 331; 540/597
See application file for complete search history.

(56) References Cited

U.S. PATENT DOCUMENTS

| | | | | |
|---|---|---|---|---|
| 5,945,431 A | * | 8/1999 | Jin et al. ............ | 514/300 |
| 6,534,520 B2 | * | 3/2003 | Bedard et al. ........ | 514/301 |
| 2002/0173507 A1 | | 11/2002 | Santora et al. | |
| 2005/0154039 A1 | | 7/2005 | Glacera et al. | |

FOREIGN PATENT DOCUMENTS

| | | |
|---|---|---|
| EP | 0446604 A | 9/1991 |
| WO | 0220484 A | 3/2002 |
| WO | 03/048154 A | 6/2003 |
| WO | 2006017672 | * 2/2006 |

OTHER PUBLICATIONS

Chan et al., Bioorganic & Medicinal Chemistry Letters (2001), 11(2), 103-105.*
Lescot, et al; Nonpeptide Urotensin II Receptor Agonists and Antagonists: Review and Structure-activity relationships Peptides, Elsevier, Amsterdam, vol. 29, No. 5, May 1, 2008 pp. 680-690, XP 022615020.
D'Sidocky, et al; Amino-substituted heterocycles, compositions thereof, and methods of treatment therewith and preparation; XP002493848, (Oct. 20, 2009).
Database Beilstein, Beilstein Institute for Organic Chemistry, Frankfurt-Main, Germany—XP002493849, (Oct. 20, 2009).

* cited by examiner

*Primary Examiner* — Niloofar Rahmani
(74) *Attorney, Agent, or Firm* — Michael P. Morris; Timothy X. Witkowski

(57) ABSTRACT

Compounds of the formula (I)

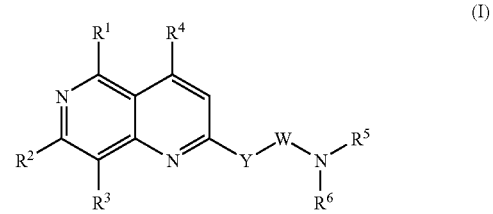

wherein $R^1$, $R^2$, $R^3$, $R^4$, $R^5$, $R^6$, W, and Y are as described herein, or a tautomer, prodrug, solvate, or salt thereof. These compounds are useful as inhibitors of Urotensin II and are thus useful for treating a variety of diseases and disorders that are mediated or sustained through the interaction of Urotensin II with its receptor, including cardiovascular diseases. This invention also relates to pharmaceutical compositions comprising these compounds, methods of using these compounds in the treatment of various diseases and disorders, processes for preparing these compounds, and intermediates useful in these processes.

3 Claims, No Drawings

UROTENSIN II RECEPTOR ANTAGONISTS

FIELD OF THE INVENTION

This invention relates to substituted [1,6]naphthyridine derivatives which are useful as inhibitors of Urotensin II and are thus useful for treating a variety of diseases and disorders that are mediated or sustained through the interaction of Urotensin II with its receptor, including cardiovascular diseases. This invention also relates to pharmaceutical compositions comprising these compounds, methods of using these compounds in the treatment of various diseases and disorders, processes for preparing these compounds, and intermediates useful in these processes.

BACKGROUND OF THE INVENTION

Urotensin II (U-II) is a cyclic peptide that was originally isolated from the goby *Gillichthys mirabilis* (H. A. Bern et al., Recent Prog. Horm. Res., 1995, 41, 533-552). U-II was found to cause smooth muscle and vascular constriction in fish as well as having effects on osmoregulation. Goby U-II was found to have variable effects on mammalian smooth muscle. For example, both vasorelaxation and vasoconstriction were observed in isolated rat aorta (A. Gibson, Br. J. Pharmacol., 1987, 91, 205-212). Subsequently, U-II was cloned from other species including man (Y. Coulouarn et al., Proc. Nat. Acad. Sci., USA, 1998, 95, 15803-15808). It was found that U-II from several species, including mammalian and non-mammalian species, contains a conserved hexapeptide core sequence although there is some variation at the amino terminus (J. M. Conlon et al., J. Exp. Zool., 1996, 275, 226-238).

The human receptor for U-II, a G Protein-coupled receptor homologous to rat GPR14 was identified in 1999 (R. S. Ames et al., Nature, 1999, 401, 282-286). The receptor (UT receptor) was found to be expressed predominantly in the cardiorenal system, although it is present in other tissues as well including skeletal muscle, adrenal gland, pancreas, thyroid, lung, liver, testis, and nervous system tissue. In blood vessels, the UT receptor was found to be expressed in cardiac and arterial tissue but not in venous tissue. Co-expression of U-II and the UT receptor in cardiovascular tissues was demonstrated in a 2001 study (M. Matsushita et al., J. Hypertens., 2001, 19, 2185-2190).

U-II was found to be a potent vasoconstrictor in isolated arteries from rats (R. S. Ames et al., 1999, ibid), humans (J. J. Maguire et al., Br. J. Pharmacol., 131, 441-446) and other species (S. A. Douglas et al., Br. J. Pharmacol., 2000, 131, 1262-1274). Consistent with the UT receptor expression pattern noted above, with few exceptions, the vasoconstrictor activity of U-II is restricted to the arterial portion of the vasculature. Evidence for a specific U-II/UT receptor interaction being responsible for the vasoconstrictor response to U-II was provided in a 2003 study which showed that the response was eliminated in blood vessels from UT receptor knock-out mice (D. J. Behm et al., Br. J. Pharmacol., 2003, 139, 464-472).

Systemic effects of U-II can vary depending on the species and method of administration. In one study, in rats, i.v. bolus administration of U-II resulted in a dose-dependent decrease of blood pressure and cardiac contractility (G. S. Hassan et al., Can. J. Physiol. Pharmacol., 2003, 81, 125-128). However, a later study showed that slow, i.v. infusion of U-II in the rat increased systemic arterial blood pressure and splanchnic vascular resistance (T. Bennet et al., Br. J. Pharmacol., 2002, 135, 200). In a study with anesthetized monkeys, systemic administration of human U-II resulted in severe myocardial depression and fatal circulatory collapse. At a 300 pmol/kg dose, peripheral resistance increased by 300% without inducing systemic hypertension (R. S. Ames et al., 1999, ibid). In healthy, human volunteers, intradermal injection of U-II resulted in a dose-dependant decrease of blood flow with sustained vasoconstriction (S. J. Leslie et al., Circulation, 2001, 102, Suppl. II, 542).

In addition to the cardiovascular effects noted above, U-II was found to have mitogenic and hypertrophic effects. In vascular smooth muscle cells from rabbit aorta, U-II was found to increase cell proliferation (V. Sauzeau et al., Circ. Res., 2001, 88, 1102-1104) through activation of Rho A and Rho kinase. In addition, U-II was found to induce cellular hypertrophy in rat cardiomyocytes (Y. Zou et al., FEBS Lett., 2001, 508, 57-60). Cellular proliferation and hypertrophy in the vasculature are associated with remodeling of blood vessel walls and myocardial tissue which occur in hypertension and heart failure.

Studies such as the ones cited above indicate that U-II has complex effects on the vasculature of the cardiorenal system and therefore may play a role in cardiovascular tone, structure and disease. In fact, clinical measurement of tissue expression or circulating and urinary levels of U-II have found up-regulation of U-II or its receptor in several cardiorenal diseases. In one study, urinary U-II concentrations in patients with hypertension or renal tubular abnormality were significantly higher than those found in normal individuals (M. Matsushita et al., 2001, ibid). In another study, U-II was found to be up-regulated in cardiomyocytes, endothelial cells and vascular smooth muscle cells of damaged heart tissue from end-stage congestive heart failure patients compared to controls. In addition, the UT receptor exhibited greater binding density in diseased tissue compared to normal (S. A. Douglas et al., Lancet, 2002, 359, 1990-1997). Furthermore, plasma levels of U-II were also found to be higher in heart failure patients than in normal controls (A. M. Richards et al., Lancet, 2002, 360, 545-546). Increased levels of U-II were also observed in patients with diabetes mellitus (K. Totsune et al., Clin. Sci., 2003, 104, 1-5) and portal hypertension and cirrhosis (J. Heller et al., J. Hepatol., 2002, 37, 767-772). The studies cited above suggest a possible role for U-II in these diseases.

In response to the physiological profile and its possible role in disease, reports of a variety of U-II receptor antagonists have appeared (see for example S. A. Douglas et al., Trends in Pharmacological Sciences, 2004, 25, 76-85; D. Dhanak et al., Ann Rep. Med. Chem., 2003, 38, 99-110). Two recent publications on the U-II receptor antagonist palosuran reported that the antagonist was able to improve survival, increase insulin, slow the increase of glycemia and delay renal damage in a streptozotocin-induced diabetic rat model (M. Clozel et al., J. Pharmacol. Exp. Ther., 2006, 316, 1115-1121) and was effective in a rat model of renal ischemia, preventing both post-ischemic renal vasoconstriction and acute renal failure (M. Clozel et al., J. Pharmacol. Exp. Ther. 2006, 316, 1115-1121 (P. Sidharta et al., Clin. Pharmacol. Ther. 2006, 80, 246-56.)). Furthermore, in a clinical trial the UT antagonist Palosuran was found to modulate the 24-hour urinary albumin excretion rate in patients by 24.3%. These studies further validate inhibition of U-II as a therapeutic target.

There remains an unmet medical need for new drugs to treat cardiovascular disease. A study published in 2003 estimated that almost 29% of the adult U.S. population had hypertension in 1999-2000 (I. Hajjar et al., JAMA, 2003, 290, 199-206). Furthermore, 69% of the hypertensive individuals studied during this period did not have their hypertension controlled at the time their blood pressure was measured. This figure was worse in patients with diabetes and hypertension where 75% of those patients studied did not have their blood pressure controlled to the target level. Another more recent study showed similar results, with less than one-third of hypertensive patients studied having blood pressure controlled to the target level (V. Andros, Am. J. Manag. Care, 2005, 11, S215-S219). Therefore, despite the number of medications available to treat hypertension, including diuretics, beta blockers, angiotensin converting enzyme inhibitors, angiotensin blockers and calcium channel blockers, hypertension remains poorly controlled or resistant to current medication for many patients. If not adequately treated, hypertension can lead to other cardiovascular diseases and organ failure including coronary artery disease, stroke, myocardial infarction, heart failure, renal failure, and peripheral artery disease.

U-II and its receptor are coexpressed in the heart and are upregulated during cardiac dysfunction. Although the expression of UT is low to undetectable in the healthy myocardium, U-II and its receptor are up-regulated in patients with moderate and end-stage heart failure. In addition, expression of UT is up-regulated in the ischemic, chronic hypoxic and post-myocardial infracted rat myocardium. Interestingly, UT up-regulation in the myocardium of hypoxic rats is accompanied by sustained ventricular hypertrophy. In vivo, short-term hypertrophic growth of cardiomyocytes is an adaptive response that increases cardiac output in cardiac dysfunction (heart failure, hypertension) and injury (myocardial infarction), whereas sustained hypertrophic growth is maladaptive and can cause adverse cardiac remodeling, which is characterized by inflammation, fibrosis, and cardiac ventricular hypertrophy. Furthermore, a UT inhibitor was found to be efficacious in a rat CHF model (N. Bousette et al., J. Mol. Cell. Cardiol. 2006, 41, 5-95; N. Bousette et al., Peptides 2006, 27, 19-2926). This study concluded that treatment with the UT antagonist provided significant reduction of overall mortality, left ventricular end-diastolic pressure, lung edema, right ventricular systolic pressure, central venous pressure, cardiomyocyte hypertrophy, and ventricular dilatation. Therefore, an orally active small molecule UT antagonist may modulate the pathological changes that occur during CHF, end-organ damage, or hypertension.

Increased expression of U-II has been shown to be associated with atherosclerosis. In humans, U-II expression (immunohistochemical staining) is increased in atherosclerotic plaques (endothelial, smooth muscle and inflammatory cells of both carotid and aortic plaques) and the increased expression correlates with disease progression (N. Bousette, et al., Athero. 2004, 176, 117-123). In atherosclerosis rodent models (apoE-/- mice) there is an upregulation of mRNA urotensin receptor (but not U-II) in the atherosclerotic aorta (Z. Wang, et al., Peptides 2006, 27, 858-863). Several in vitro studies have demonstrated a functional role for U-II in atherosclerosis pathology. U-II may play a novel role in the formation of macrophage-derived foam cells by upregulating ACAT-1 expression via the UT receptor/G-protein/c-Src/PKC/MEK and ROCK pathways but not by SR-A, thus contributing to the relatively rapid development of atherosclerosis in hypertension (T. Wantanabe, et al., Hypertension 2005, 46, 738-744). U-II and 5-HT may induce the synergistic interaction in inducing VSMC proliferation via a G-protein-coupled receptor/PKC/Src tyrosine kinase/MAPK pathway, thus contributing to the relatively rapid development of atherosclerosis in hypertensive vascular disease (J. Hypertension 19, 2191-2196). U-II acts synergistically with moxLDL in inducing VSMC proliferation via the c-Src/PKC/MAPK pathway, which may explain the relatively rapid progression of atherosclerosis in patients with hypertension and hypercholesterolemia (T. Wantanabe, et al., Circulation 2001, 104, 16-18, 2001).

BRIEF SUMMARY OF THE INVENTION

In a general aspect, the present invention is directed to the compounds of the following formula (I):

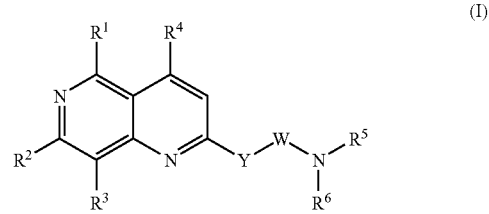

wherein $R^1$, $R^2$, $R^3$, $R^4$, $R^5$, $R^6$, Y, and W are as defined herein, as well as the tautomers thereof, and salts thereof. It has been found that the compounds of formula (I) have valuable pharmacological properties, particularly an inhibiting activity of U-II.

In another aspect, the present invention is directed to a method of inhibiting U-II activity in an individual comprising administering to the individual a compound described above.

In another aspect, the present invention is directed to a method of treating a disease or disorder associated with the activation of U-II comprising administering to an individual a compound described above.

In another aspect, the present invention is directed to a method of treating a cardiovascular or related disease comprising administering to an individual a compound described above. Examples of such diseases that may be treated include, for example, hypertension, stroke, heart failure, renal disease, myocardial infarction, coronary artery disease, peripheral artery disease, and atherosclerosis.

In another aspect, the present invention is directed to a method of treating diabetes or cirrhosis comprising administering to an individual a compound described above.

In yet additional aspects, the present invention is directed to pharmaceutical compositions comprising the abovementioned compounds, processes for preparing the above-mentioned compounds, and intermediates used in these processes.

DETAILED DESCRIPTION OF THE INVENTION

In an embodiment, there are provided compounds of the formula (I)

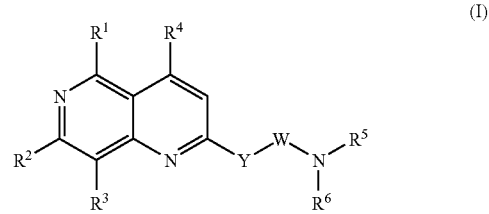

wherein:
$R^1$, $R^2$, $R^3$, and $R^4$ are each independently H, $C_{1-6}$-alkyl, $C_{1-6}$-alkoxy, aryl, or heteroaryl;
Y is —N($R_8$)—, —N($R_8$)C(O)N($R_9$)—, —N($R_8$)C(O)—, —C(O)N($R_8$)—, —N($R_8$)SO$_2$—, —O—, or —S—;

W is —(CH$_2$)$_n$—, wherein each methylene group is optionally independently substituted with one or two C$_{1-3}$-alkyl groups and n is 0 to 4;

R$^5$ and R$^6$ are each independently H, C$_{1-6}$-alkyl, —CO$_2$—C$_{1-6}$-alkyl, aryl-C$_{0-4}$-alkyl, or heteroaryl-C$_{0-4}$-alkyl, wherein each aryl or heteroaryl is optionally independently substituted with one to three R$^7$, or R$^5$ and R$^6$, together with the N they are bonded to, are a heterocyclyl group optionally substituted with one to three groups selected from aryl, arylamino, aryl-C$_{1-4}$-alkyl, aryl-C$_{0-1}$-alkyl-C(O)—, aryl-C$_{0-1}$-alkyl-SO$_2$—, —N(R$_8$)SO$_2$—C$_{0-1}$-alkylaryl, —N(R$_8$)SO$_2$—C$_{0-1}$-heteroaryl, —SO$_2$N(R$_8$)-aryl, —SO$_2$N(R$_8$)-heteroaryl, aryl-C$_{0-4}$-alkyloxy, diarylhydroxy-C$_{1-3}$-alkyl, diarylmethoxy, heteroaryl, heteroarylamino, heteroaryl-C$_{1-4}$-alkyl, heteroarylSO$_2$—, heteroaryl-C$_{0-4}$-alkyloxy, heteroaryl-C(O)N(R$_8$)—, heteroaryl-N(R$_8$)C(O)—, C$_{1-6}$-alkyl, C$_{1-6}$-alkoxy, C$_{1-6}$-alkyl-SO$_2$—, —CO$_2$—C$_{1-6}$-alkyl, OH, oxo, and halogen, wherein each aryl, heteroaryl, or alkyl group is optionally substituted with one to three R$_7$;

R$_7$ is C$_{1-6}$-alkyl, C$_{1-6}$-alkenyl, C$_{1-6}$-alkoxy, C$_{1-6}$-alkylamino, di(C$_{1-6}$-alkyl)amino, halogen, —OH, —CN, —CF$_3$, —OCF$_3$, —CO$_2$H, —CO$_2$—C$_{1-6}$-alkyl, —C(O)—C$_{1-6}$-alkyl, —SO$_2$—C$_{1-6}$-alkyl, —S—C$_{1-6}$-alkyl, —NHC(O)—C$_{1-6}$-alkyl, —NHSO$_2$—C$_{1-6}$-alkyl, —C(O)N(R$_8$)(R$_9$), —NO$_2$, or SO$_2$N(R$_8$)(R$_9$); and R$_8$ and R$_9$ are each independently H or C$_{1-6}$-alkyl, or a tautomer, prodrug, solvate, or salt thereof.

Another aspect of the invention includes compounds of formula (I) wherein:

R$^1$ and R$^2$ are each independently H, C$_{1-6}$-alkyl, C$_{1-6}$-alkoxy, or phenyl;

R$^3$ and R$^4$ are each H;

Y is —NH—, —NHC(O)NH—, —NHC(O)—, —C(O)NH—, —NHSO$_2$—, —O—, or —S—;

W is —(CH$_2$)$_n$—, wherein each methylene group is optionally independently substituted with one or two C$_{1-3}$-alkyl groups and n is 0 to 4;

R$^5$ and R$^6$ are each independently H, C$_{1-6}$-alkyl, phenyl-C$_{1-4}$-alkyl, or pyridyl-C$_{0-4}$-alkyl, wherein each phenyl or pyridyl is optionally independently substituted with one to three R$^7$, or R$^5$ and R$^6$, together with the N they are bonded to, are a pyrrolidinyl, piperidinyl, piperazinyl, morpholinyl, azepanyl, or imidazolyl group, each optionally independently substituted with one to three groups selected from phenyl, phenylamino, phenyl-C$_{1-4}$-alkyl, phenyl-C$_{0-1}$-alkyl-SO$_2$—, benzhydryl-C$_{0-1}$-alkylSO$_2$—, -benzhydryl-CH$_2$C(O)—, —NHSO$_2$-phenyl, —SO$_2$NH-phenyl, —SO$_2$NH-benzhydryl, phenyl-C$_{0-4}$-alkyloxy, diphenylhydroxymethyl, diphenylmethoxy, naphthyridinyl, pyridyl, pyrimidinyl, pyrazinyl, pyridylamino, pyrimidinylamino, pyrazinylamino, pyridyloxy, pyrimidinyloxy, pyrazinyloxy, pyridylmethyl, pyrimidinylmethyl, pyrazinylmethyl, C$_{1-6}$-alkyl, —C$_{1-6}$-alkyl-SO$_2$—, —C$_{1-6}$-alkoxy, —CO$_2$—C$_{1-6}$-alkyl, OH, oxo, and halogen, wherein each phenyl, pyridyl, pyrimidinyl, pyrazolyl, or alkyl group is optionally independently substituted with one to three R$_7$; and R$_7$ is C$_{1-6}$-alkyl, C$_{1-6}$-alkenyl, C$_{1-6}$-alkoxy, C$_{1-6}$-alkylamino, di(C$_{1-6}$-alkyl)amino, halogen, —OH, —CN, CF$_3$, —OCF$_3$, —CO$_2$H, —CO$_2$—C$_{1-6}$-alkyl, —C(O)—C$_{1-6}$-alkyl, —SO$_2$—C$_{1-6}$-alkyl, —S—C$_{1-6}$-alkyl, —NHC(O)—C$_{1-6}$-alkyl, —NHSO$_2$—C$_{1-6}$-alkyl, —C(O)NH$_2$, —NO$_2$, or SO$_2$NH$_2$, or a tautomer, prodrug, solvate, or salt thereof.

A further aspect of the invention includes compounds of formula (I) wherein:

R$^1$ and R$^2$ are each independently H or C$_{1-6}$-alkyl;

R$^3$ and R$^4$ are each H;

Y is —NH—, —N(CH$_3$)—, or —NHC(O)NH—;

W is —(CH$_2$)$_n$—, wherein n is 0 to 3;

R$^5$ and R$^6$ are each independently H, C$_{1-6}$-alkyl, or phenyl optionally independently substituted with one to three R$^7$, or R$^5$ and R$^6$, together with the N they are bonded to, are pyrrolidinyl, piperidinyl, piperazinyl, morpholinyl, or azepanyl group, each optionally independently substituted with one to three groups selected from phenyl, phenyl-C$_{1-3}$-alkyl, phenyl-SO$_2$—, benzhydryl-C$_{0-1}$-alkyl-SO$_2$—, -benzhydryl-CH$_2$C(O)—, —SO$_2$NH-benzhydryl, phenyl-C$_{0-1}$-alkyloxy, diphenylhydroxymethyl, diphenylmethoxy, C$_{1-6}$-alkyl, —C$_{1-6}$-alkylSO$_2$—, C$_{1-6}$-alkoxy, —CO$_2$—C$_{1-6}$-alkyl and OH, wherein each phenyl is optionally independently substituted with one to three R$_7$; and R$_7$ is C$_{1-6}$-alkyl, C$_{1-6}$-alkoxy, Cl, F, —OH, —OCF$_3$, or CF$_3$, or a tautomer, prodrug, solvate, or salt thereof.

Yet another aspect of the invention includes compounds of formula (I) wherein:

R$^1$ is C$_{1-3}$-alkyl;

R$^2$, R$^3$, and R$^4$ are each H;

Y is —NH—;

W is —(CH$_2$)$_n$—, wherein n is 2 or 3;

R$^5$ and R$^6$, together with the N they are bonded to, are a pyrrolidinyl, piperidinyl, piperazinyl, morpholinyl, or azepanyl group, each optionally independently substituted with one to three groups selected from phenyl, phenyl-C$_{1-3}$-alkyl, phenyl-SO$_2$—, phenyl-C$_{0-1}$-alkyloxy, diphenylhydroxymethyl, diphenylmethoxy, C$_{1-3}$-alkyl, —CO$_2$C$_{1-6}$-alkyl, and OH, wherein each phenyl is optionally independently substituted with one to three R$_7$; and R$_7$ is C$_{1-6}$-alkyl, C$_{1-6}$-alkoxy, Cl, F, —OH, —OCF$_3$, or CF$_3$, or a tautomer, prodrug, solvate, or salt thereof.

The following are representative compounds of Formula (I) according to the invention:

| Compound Name | Compound Structure |
| --- | --- |
| 5-Methyl-2-((R)-1-methylpyrrolidin-3-yloxy)-[1,6]naphthyridine | Chiral |

-continued

| Compound Name | Compound Structure |
| --- | --- |
| Dimethyl-[2-(5-methyl[1,6]naphthyridin-2-yloxyethyl]amine | 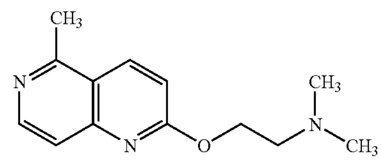 |
| [2-(4-Benzylpiperidin-1-yl)ethyl]-(5-methyl[1,6]naphthyridin-2-yl)amine | 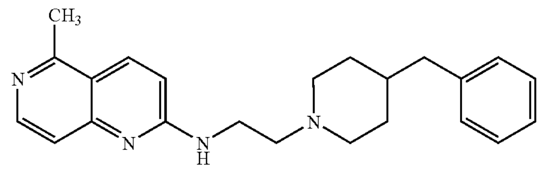 |
| (5-Methyl[1,6]naphthyridin-2-yl)-(2-piperidin-1-ylethyl)amine | 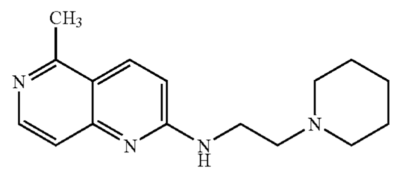 |
| 1-[2-(5-Methyl[1,6]naphthyridin-2-ylamine)ethyl]piperidin-4-ol | 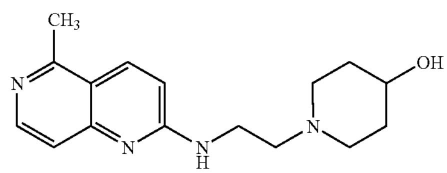 |
| 4-Benzyl-1-[2-(5-methyl[1,6]naphthyridin-2-ylamino)ethylpiperidin-4-ol | 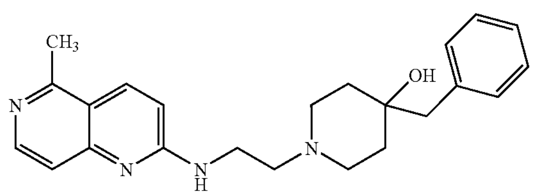 |
| 4-[2-(5-Methyl[1,6]naphthyridin-2-ylaminoethyl]piperazine-1-carboxylic acid tert-butyl ester | 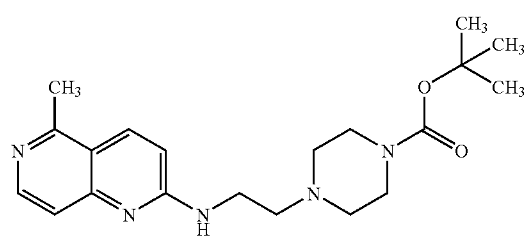 |
| (5-Methyl[1,6]naphthyridin-2-yl)-(2-piperazin-1-ylethyl)amine | 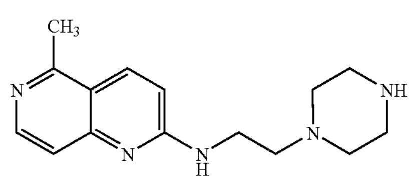 |
| [2-(4-Benzylpiperazin-1-yl)ethyl]-(5-methyl[1,6]naphthyridin-2-yl)amine | 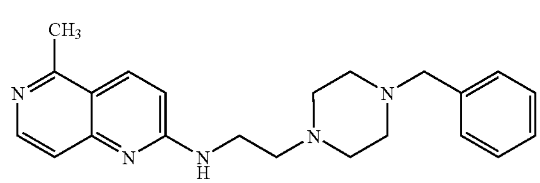 |

-continued

| Compound Name | Compound Structure |
|---|---|
| {2-[4-(4-Chlorophenyl)piperazin-1-yl]ethyl}-(5-methyl-1-[1,6]naphthyridin-2-yl)amine | 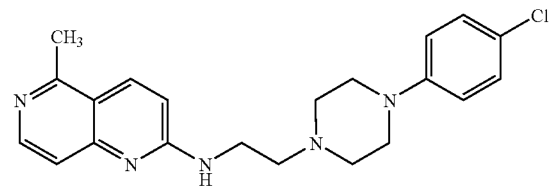 |
| [2-(4-Benzenesulfonylpiperazin-1-yl)ethyl]-(5-methyl[1,6]naphthyridin-2-yl)amine | 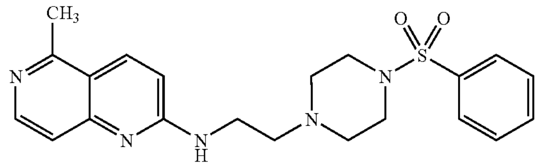 |
| (5-Methyl[1,6]naphthyridin-2-yl{2-[4-(3-phenylpropyl)piperazin-1-yl]ethyl}amine | 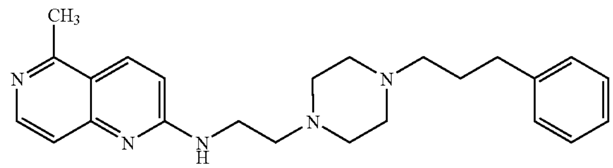 |
| (5-Methyl[1,6]naphthyridin-2-yl)-[2-(4-phenethylpiperazin-1-yl)ethyl]amine | 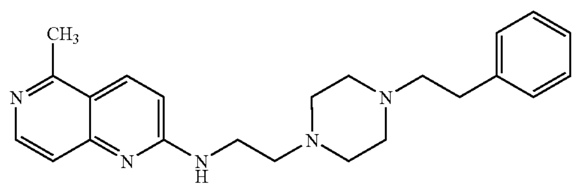 |
| [2-(4-Benzylpiperidin-1-yl)ethyl]-5,7-dimethyl[1,6]naphthyridin-2-yl)amine | 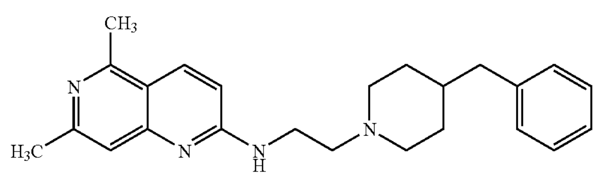 |
| [2-(4-Benzenesulfonylpiperazin-1-yl)ethyl]-(5,7-dimethyl[1,6]naphthyridin-2-yl)amine | 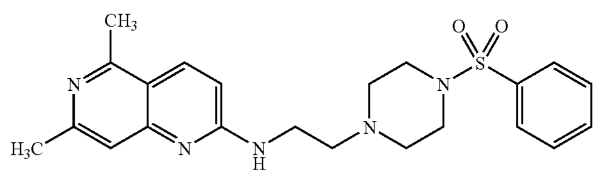 |
| 5-Methyl-2-((S)-1-methylpyrrolidin-2-ylmethoxy)-[1,6]naphthyridine | 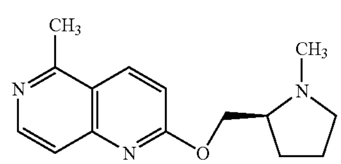 |
| [2-(4-Benzylpiperidin-1-yl)ethyl]-(5-phenyl[1,6]naphthyridin-2-yl)amine | 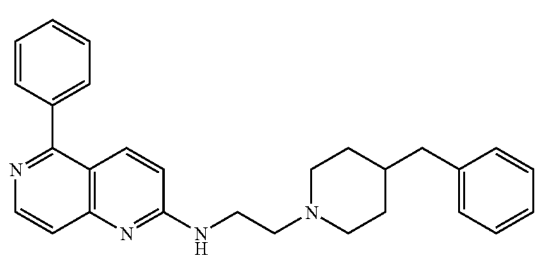 |

| Compound Name | Compound Structure |
|---|---|
| N,N-Dimethyl-N'-(5-methyl[1,6]naphthyridin-2-yl)ethane-1,2-diamine | 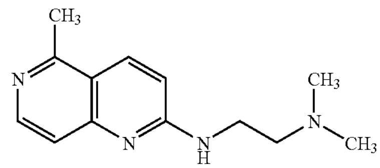 |
| [2-(4-Benzylpiperidin-1-yl)ethyl]-(5-isopropyl[1,6]naphthyridin-2-yl)amine | 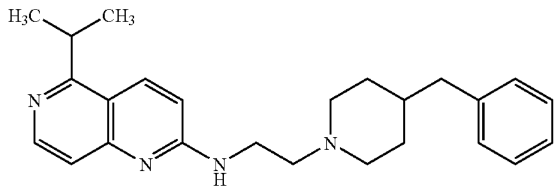 |
| [2-(4-Benzylpiperidin-1-yl)ethyl]-(5-ethyl[1,6]naphthyridin-2-yl)amine | 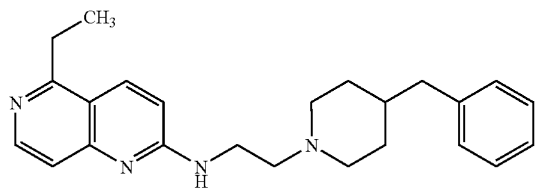 |
| [2-(4-Benzylpiperidin-1-yl)ethyl]-[1,6]naphthyridin-2-ylamine | 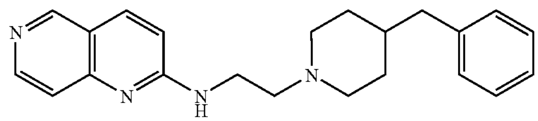 |
| 2-[3-(4-Benzylpiperidin-1-yl)propoxy]-5-methyl[1,6]naphthyridine | 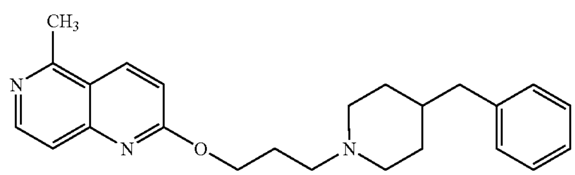 |
| [2-(4-Benzylpiperidin-1-yl)ethyl]-(7-methyl[1,6]naphthyridin-2-yl)amine | 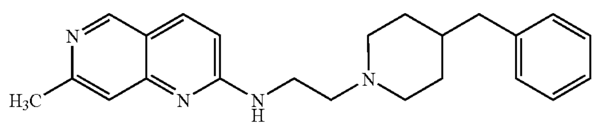 |
| (5-Methyl[1,6]naphthyridin-2-yl)-[2-(4-phenethylpiperidin-1-yl)ethyl]amine | 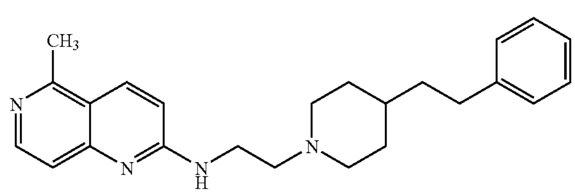 |
| 5-Methyl-2-(2-piperidin-1-ylethoxy)-[1,6]naphthyridine | 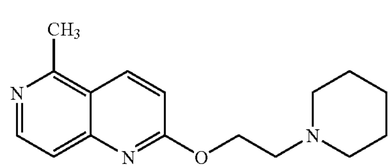 |
| 5-Methyl-2-(2-pyrrolidin-1-ylethoxy)-[1,6]naphthyridine | 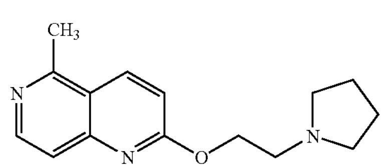 |

-continued

| Compound Name | Compound Structure |
|---|---|
| Benzylmethyl-[2-(5-methyl[1,6]naphthyridin-2-yloxy)ethyl]amine | 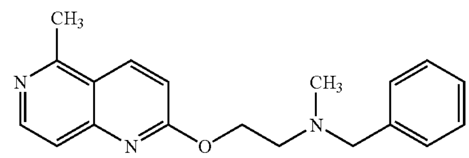 |
| Dimethyl-[2-(5-methyl[1,6]naphthyridin-2-yloxy)propyl]amine | 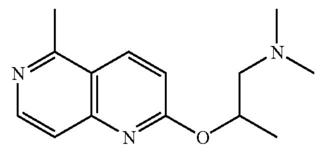 |
| [2,2-Dimethyl-3-(5-methyl[1,6]naphthyridin-2-yloxy)propyl]dimethylamine | 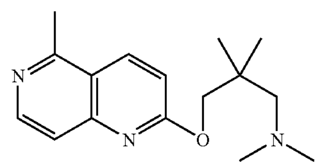 |
| 2-(1-Benzylpiperidin-4-yloxy)-5-methyl[1,6]naphthyridine | 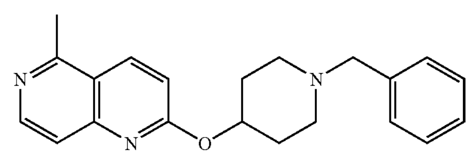 |
| 2-(1-Benzylpiperidin-3-yloxy)-5-methyl[1,6]naphthyridine | 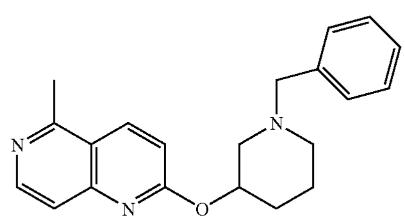 |
| 5-Methyl-2-(2-morpholin-4-ylethoxy)-[1,6]naphthyridine | 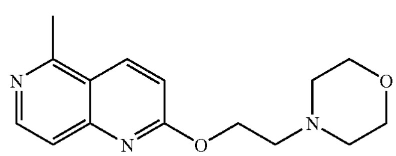 |
| 2-(1-Isopropylpyrrolidin-3-yloxy)-5-methyl[1,6]naphthyridine | 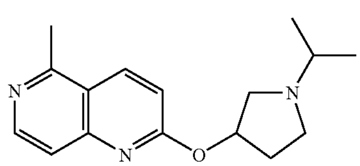 |
| 2-(1-Ethylpyrrolidin-3-yloxy)-5-methyl[1,6]naphthyridine | 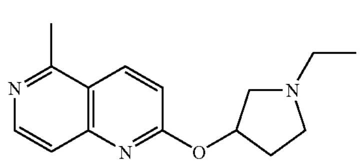 |

-continued

| Compound Name | Compound Structure |
|---|---|
| 2-((S)-1-Benzylpyrrolidin-2-ylmethoxy)-5-methyl[1,6]naphthyridine | Chiral |
| 1-[2-(5-Methyl[1,6]naphthyridin-2-yloxy)ethyl]imidazolidin-2-one | 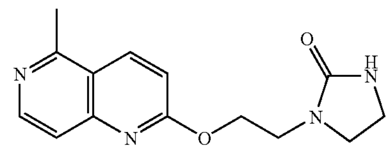 |
| 5-Methyl-2-[2-(4-methylpiperazin-1-yl)ethoxy]-[1,6]naphthyridine | 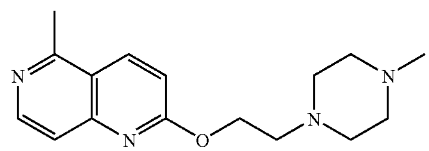 |
| 5-Methyl-2-[3-(4-methylpiperazin-1-yl)propoxy]-[1,6]naphthyridine | 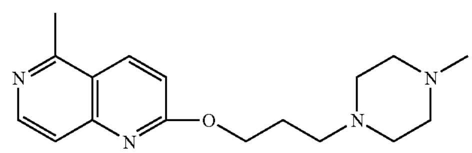 |
| 2-[2-(4-Benzylpiperidin-1-yl)ethoxy]-5-methyl[1,6]naphthyridine | 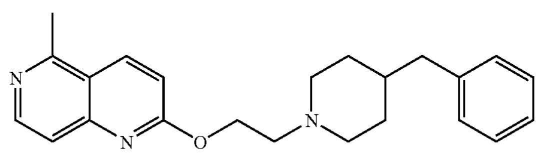 |
| [2-(4-Benzylpiperidin-1-yl)ethyl]-(5-methoxy-7-methyl[1,6]naphthyridin-2-yl)amine | 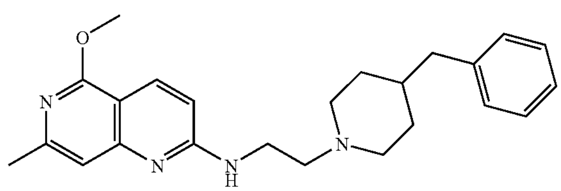 |
| [2-(4-Benzyloxypiperidin-1-yl)ethyl]-(5-methyl[1,6]naphthyridin-2-yl)amine | 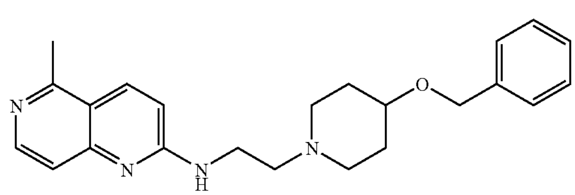 |
| (5-Methyl[1,6]naphthyridin-2-yl)-(3-morpholin-4-ylpropyl)amine | 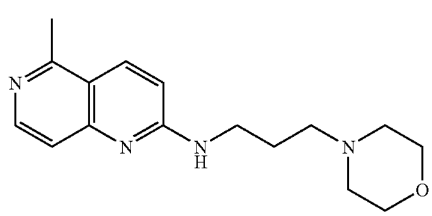 |

-continued

| Compound Name | Compound Structure |
|---|---|
| ((S)-1-Benzylpyrrolidin-3-yl)-(5-methyl[1,6]naphthyridin-2-yl)amine | Chiral 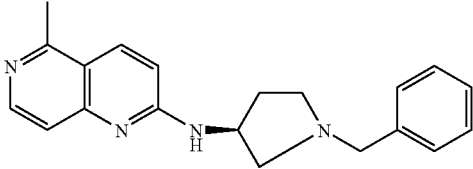 |
| 2,2,N,N-Tetramethyl-N'-(5-methyl[1,6]naphthyridin-2-yl)propane-1,3-diamine | 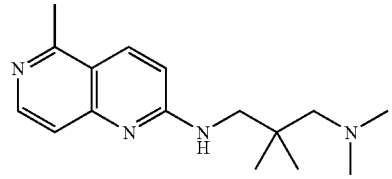 |
| N,N-Dimethyl-N'-(5-methyl[1,6]naphthyridin-2-yl)propane-1,3-diamine | 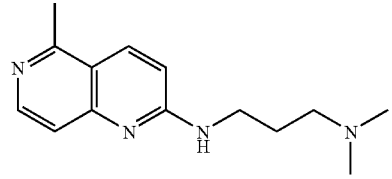 |
| 1-(Ethylpyrrolidin-2-ylmethyl)-(5-methyl[1,6]naphthyridin-2-yl)amine | 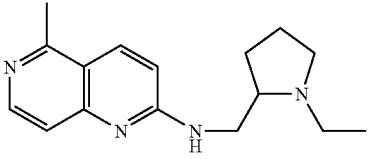 |
| (5-Methyl[1,6]naphthyridin-2-yl)-2-pyrrolidin-1-ylethyl)amine | 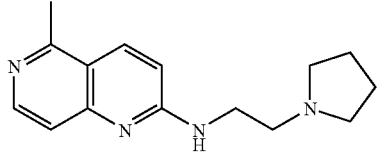 |
| 1-[3-(5-Methyl[1,6]naphthyridin-2-ylamino)propyl]pyrrolidin-2-one | 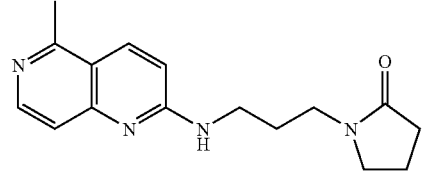 |
| N,N-Diisopropyl-N'-(5-methyl[1,6]naphthyridin-2-yl)ethane-1,2-diamine | 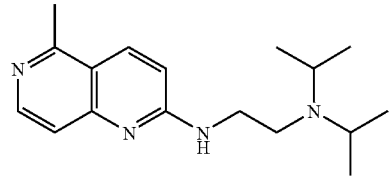 |
| 1-[2-(5-Methyl[1,6]naphthyridin-2-ylamino)ethyl]pyrrolidin-2-one | 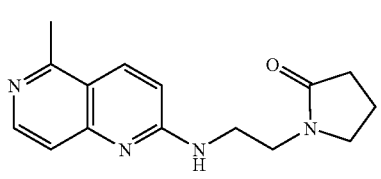 |

-continued

| Compound Name | Compound Structure |
|---|---|
| (2-Azepan-1-ylethyl)-(5-methyl[1,6]naphthyridin-2-yl)amine | 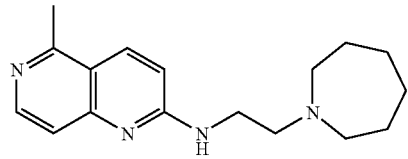 |
| (1-Benzylpyrrolidin-3-yl)-(5-methyl-[1,6]naphthyridin-2-yl)amine | 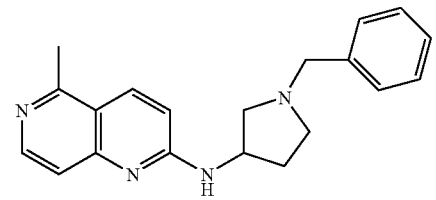 |
| (5-Methyl[1,6]naphthyridin-2-yl)-[3-(4-methylpiperazin-1-yl)propyl]amine | 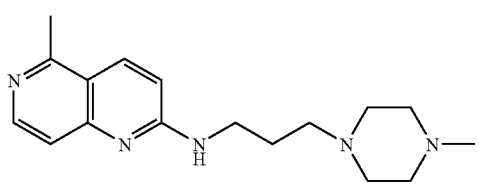 |
| (5-Methyl[1,6]naphthyridin-2-yl)-[2-(2-methylpyrrolidin-1-yl)ethyl]amine | 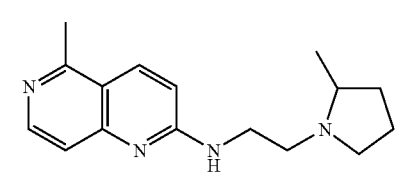 |
| (3-Azepan-1-ylpropyl)-(5-methyl[1,6]naphthyridin-2-yl)amine | 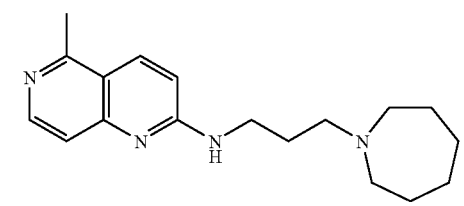 |
| [3-(4-Benzylpiperidin-1-yl)propyl]-(5-methyl[1,6]naphthyridin-2-yl)amine | 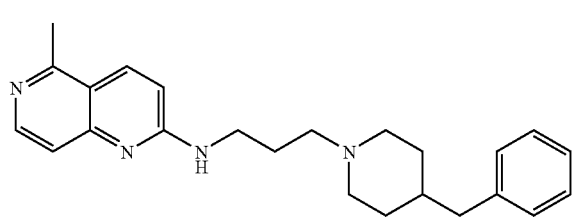 |
| (5-Methyl[1,6]naphthyridin-2-yl)-[3-(2-methylpiperidin-1-yl)propyl]amine | 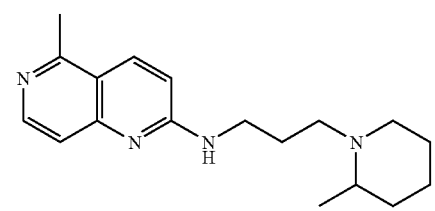 |
| (5-Methyl[1,6]naphthyridin-2-yl)-(3-piperidin-1-ylpropyl)amine | 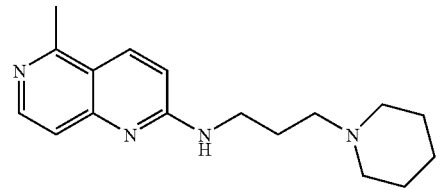 |

-continued

| Compound Name | Compound Structure |
|---|---|
| 2-(4-Benzylpiperidin-1-yl)ethyl]methyl-(5-methyl[1,6]naphthyridin-2-yl)amine | 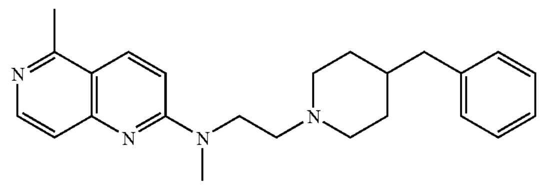 |
| [3-(2,6-Dimethylpiperidin-1-yl)propyl]-(5-methyl[1,6]naphthyridin-2-yl)amine | 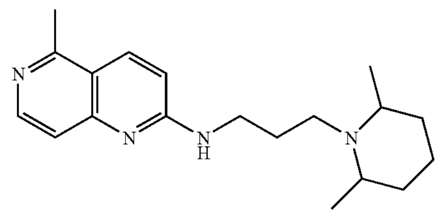 |
| 2-(4-Benzylpiperidin-1-yl)-N-(5-methyl[1,6]naphthyridin-2-yl)acetamide | 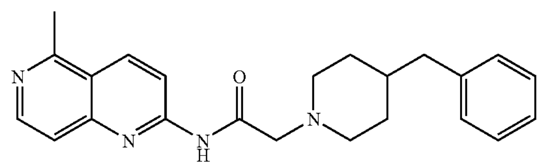 |
| {2-[4-(4-Fluorophenoxy)piperidin-1-yl]ethyl}-(5-methyl[1,6]naphthyridin-2-yl)amine | 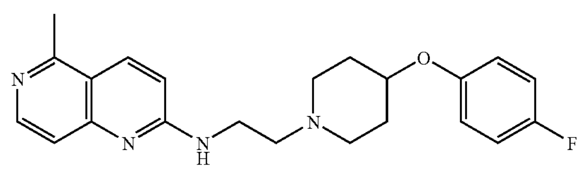 |
| (5-Methyl[1,6]naphthyridin-2-yl)-{2-[4-(4-trifluoromethylphenoxy)piperidin-1-yl]ethyl}amine | 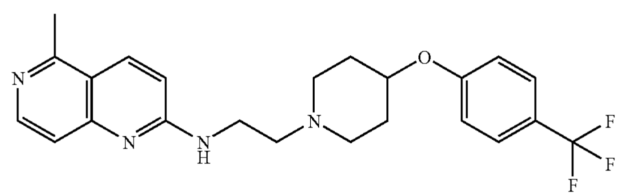 |
| N-(5-Methyl[1,6]naphthyridin-2-yl)-2-[4-(pyrimidin-2-yloxy)piperidin-1-yl]acetamide | 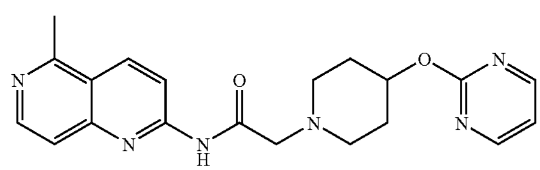 |
| N-(5-Methyl[1,6]naphthyridin-2-yl)-2-[4-(pyrimidin-2-ylamino)piperidin-1-yl]acetamide | 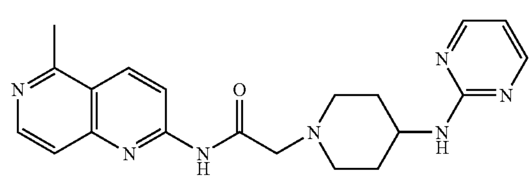 |
| [2-(1-Benzylpiperidin-4-yl)ethyl]-(5-methyl[1,6]naphthyridin-2-yl)amine | 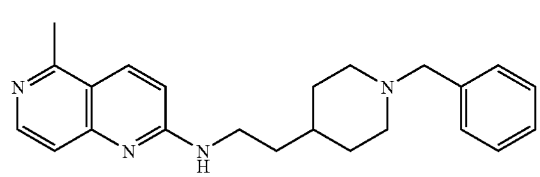 |

-continued

| Compound Name | Compound Structure |
|---|---|
| {1-[2-(5-Methyl[1,6]naphthyridin-2-ylamino)ethyl]piperidin-4-yl}diphenylmethanol | 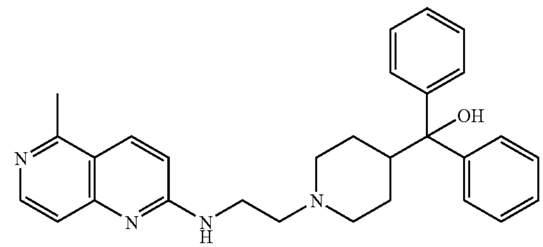 |
| 1-[2-(4-Benzylpiperidin-1-yl)ethyl]-3-(5-methyl[1,6]naphthyridin-2-yl)urea | 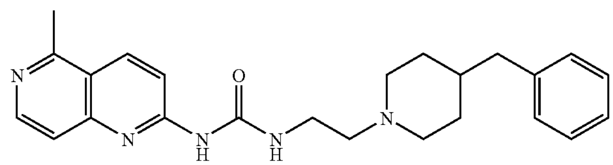 |
| [2-(4-Benzhydryloxypiperidin-1-yl)ethyl]-(5-methyl[1,6]naphthypyridin-2-yl)amine | 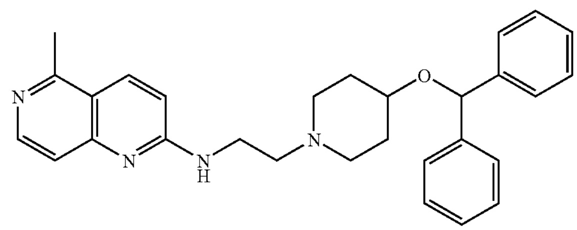 |
| {2-[4-(3,5-Dimethoxybenzyloxy)piperidin-1-yl]ethyl}-(5-methyl[1,6]naphthyridin-2-yl)amine | 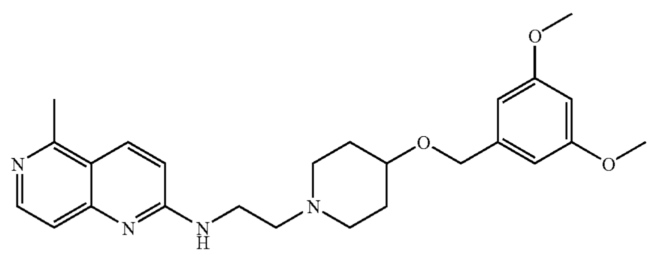 |
| (5-Methyl[1,6]naphthyridin-2-yl)-{2-[4-(5-methyl[1,6]naphthyridin-2-yl)piperazin-1-yl]ethyl}amine | 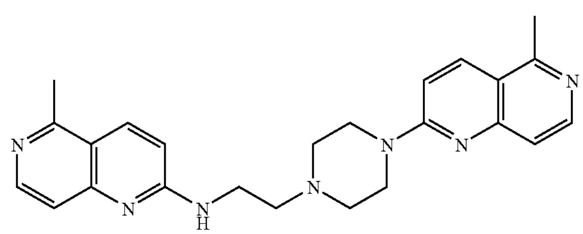 |
| (5-Methyl[1,6]naphthyridin-2-yl)-{2-[4-(3-phenylpropyl)piperidin-1-yl]ethyl}amine | 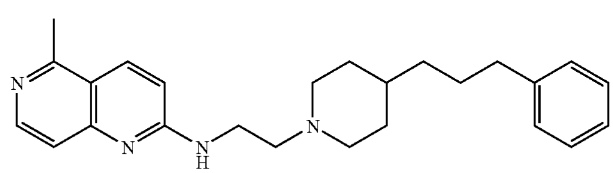 |
| 1-[2-(5-Methyl[1,6]naphthyridin-2-ylamino)ethyl]piperidin-3-ol | 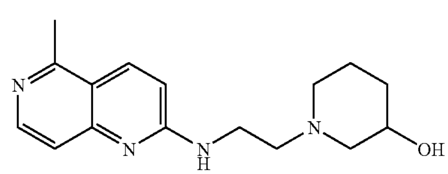 |

| Compound Name | Compound Structure |
|---|---|
| (5-Methyl[1,6]naphthyridin-2-yl)-{2-[4-(4-trifluoromethylbenzenesulfonyl)piperazin-1-yl]ethyl}amine | 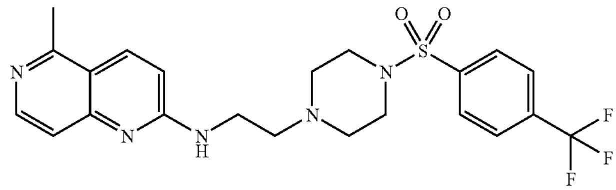 |
| 4-{4-[2-(5-Methyl[1,6]naphthyridin-2-ylamino)ethyl]piperazine-1-sulfonyl}benzonitrile | 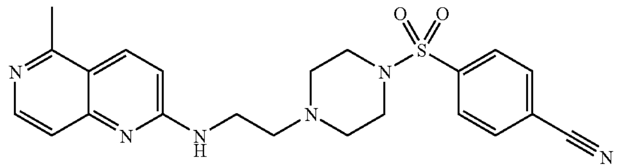 |
| {2-[4-(4-Fluorobenzenesulfonyl)piperazin-1-yl]ethyl}-(5-methyl[1,6]naphthyridin-2-yl)amine | 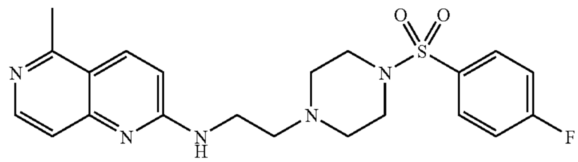 |
| {2-[4-(4-Methoxybenezenesulfonyl)piperazin-1-yl]ethyl}-(5-methyl[1,6]naphthyridin-2-yl)amine | 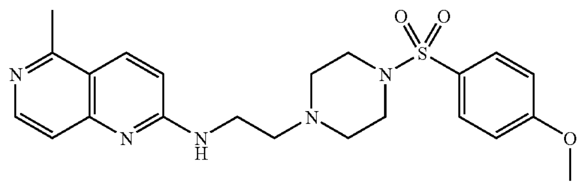 |
| {2-[4-(6-Chloropyridine-3-sulfonyl)piperazin-1-yl]ethyl}-(5-methyl[1,6]naphthyridin-2-yl)amine | 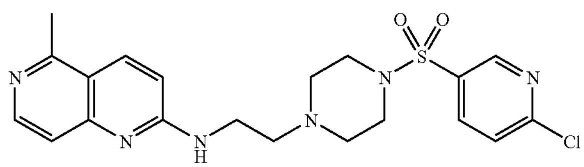 |
| [2-(4-Methanesulfonylpiperazin-1-yl)ethyl]-(5-methyl[1,6]naphthyridin-2-yl)amine | 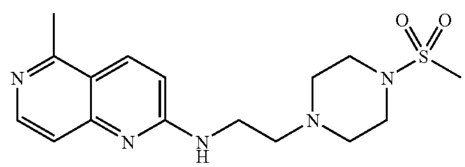 |
| (5-Methyl[1,6]naphthyridin-2-yl)-[2-(4-phenylmethanesulfonylpiperazin-1-yl)ethyl]amine | 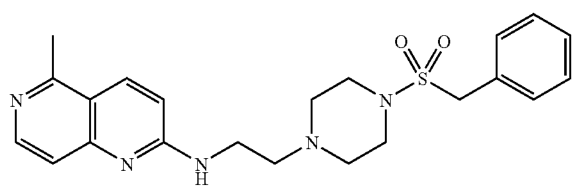 |
| {2-[4-(4-Bromobenzenesulfonyl)piperazin-1-yl]ethyl}-(5-methyl[1,6]naphthyridin-2-yl)amine | 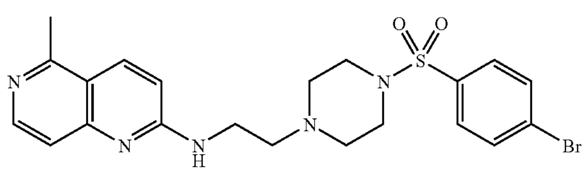 |
| {2-[4-(4-Chlorobenzenesulfonyl)piperazin-1-yl]ethyl}-(5-methyl[1,6]naphthyridin-2-yl)amine | 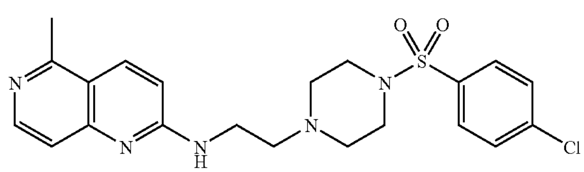 |

-continued

| Compound Name | Compound Structure |
|---|---|
| {2-[4-(4-Methanesulfonylbenzenesulfonyl)piperazin-1-yl]ethyl}-(5-methyl[1,6]naphthyridin-2-yl)amine | 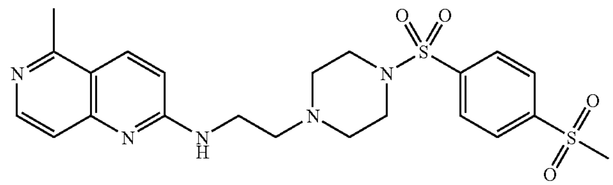 |
| {2-[4-(4-tert-Butylbenzenesulfonyl)piperazin-1-yl]ethyl}-(5-methyl[1,6]naphthyridin-2-yl)amine | 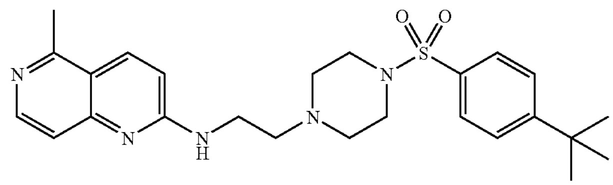 |
| (5-Methyl[1,6]naphthyridin-2-yl)-{2-[4-(2,4,6-trichlorobenzenesulfonyl)piperazin-1-yl]ethyl}amine | 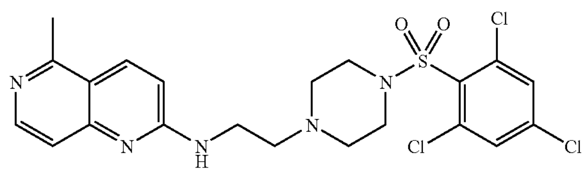 |
| (5-Methyl[1,6]naphthyridin-2-yl)-{2-[4-(2-trifluoromethoxybenzenesulfonyl)piperazin-1-yl]ethyl}amine | 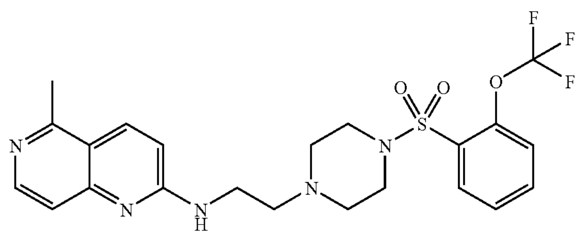 |
| (5-Methyl[1,6]naphthyridin-2-yl)-{2-[4-(3-trifluoromethoxybenzenesulfonyl)piperazin-1-yl]ethyl}amine | 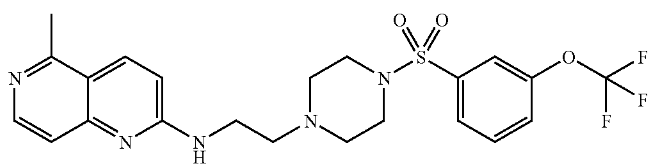 |
| (5-Methyl[1,6]naphthyridin-2-yl)-{2-[4-(4-trifluoromethoxybenzenesulfonyl)piperazin-1-yl]ethyl}amine | 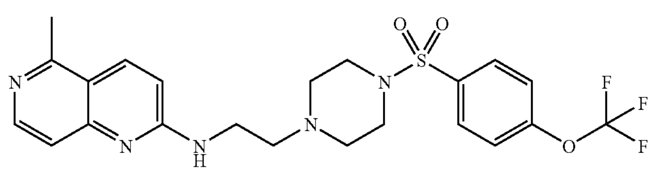 |
| {2-[4-(4-Fluorobenzenesulfonyl)piperidin-1-yl]ethyl}-(5-methyl[1,6]naphthyridin-2-yl)amine | 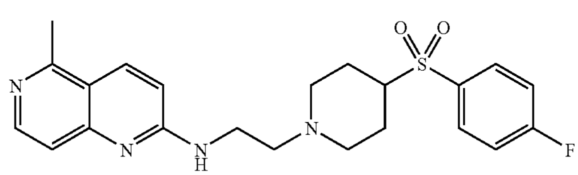 |
| N-{1-[2-(5-Methyl[1,6]naphthyridin-2-ylamino)ethyl]piperidin-4-yl}-C-phenylmethanesulfonamide | 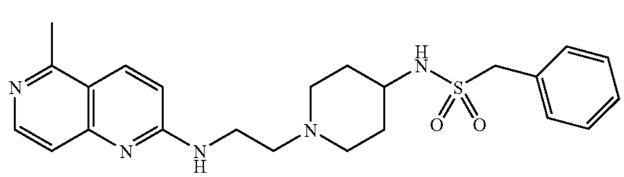 |

| Compound Name | Compound Structure |
|---|---|
| N-{1-[2-(5-Methyl[1,6]naphthyridin-2-ylamino)ethyl]piperidin-4-yl}benzenesulfonamide | 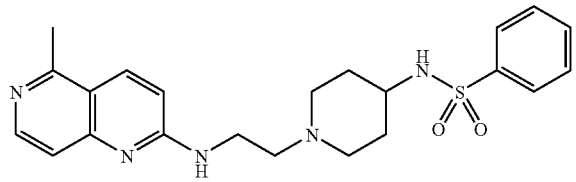 |
| N-{1-[2-(5-Methyl[1,6]naphthyridin-2-ylamino)ethyl]piperidin-4-yl}-4-trifluoromethylbenzenesulfonamide | 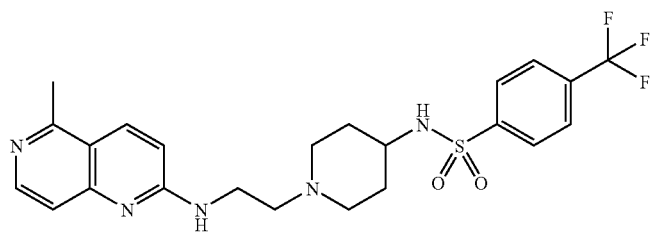 |
| {2-[3-(4-Fluorobenzenesulfonyl)piperidin-1-yl]ethyl}-(5-methyl[1,6]naphthyridin-2-yl)amine | 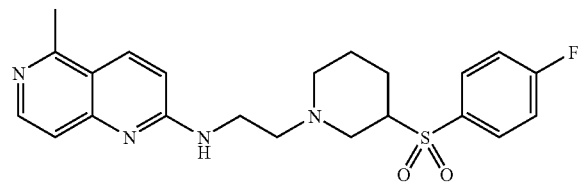 |
| 1-[2-(5-Methyl[1,6]naphthyridin-2-ylamino)ethyl]piperidine-4-sulfonic acid benzhydrylamide | 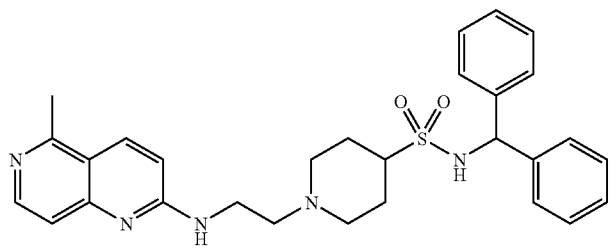 |
| {2-[3-(4-Fluorobenzenesulfonyl)pyrrolidin-1-yl]ethyl}-(5-methyl[1,6]naphthyridin-2-yl)amine | 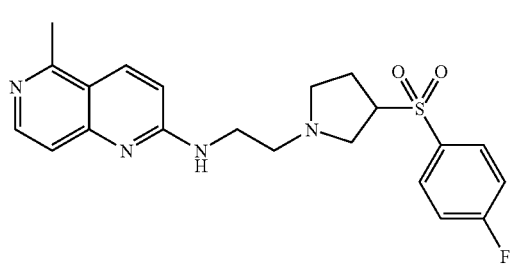 |
| {2-[4-(2,2-Diphenylethanesulfonyl)piperazin-1-yl]ethyl}-(5-methyl[1,6]naphthyridin-2-yl)amine | 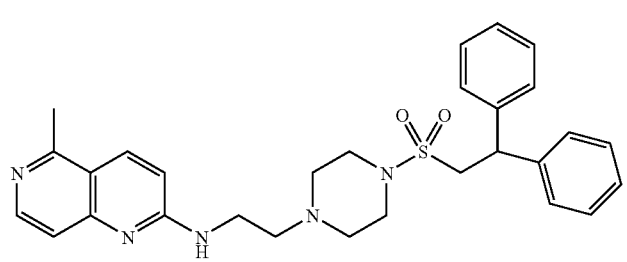 |

| Compound Name | Compound Structure |
|---|---|
| {2-[4-(Diphenylmethanesulfonyl)piperazin-1-yl]ethyl}-(5-methyl[1,6]naphthyridin-2-yl)amine | 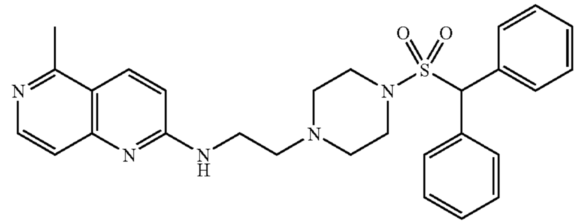 |
| 1-{4-[2-(5-Methyl[1,6]naphthyridin-2-ylamino)ethyl]piperazin-1-yl}-3,3-diphenylpropan-1-one | | or a tautomer, prodrug, solvate, or salt thereof.

Preferred compounds of formula (I) include the following:

[2-(4-Benzylpiperidin-1-yl)ethyl]-(5-methyl[1,6]naphthyridin-2-yl)amine;
(5-Methyl[1,6]naphthyridin-2-yl)-(2-piperidin-1-ylethyl)amine;
1-[2-(5-Methyl[1,6]naphthyridin-2-ylamine)ethyl]piperidin-4-ol;
4-Benzyl-1-[2-(5-methyl[1,6]naphthyridin-2-ylamino)ethyl]piperidin-4-ol;
4-[2-(5-Methyl[1,6]naphthyridin-2-ylaminoethyl]piperazine-1-carboxylic acid tert-butyl ester;
[2-(4-Benzylpiperazin-1-yl)ethyl]-(5-methyl[1,6]naphthyridin-2-yl)amine;
{2-[4-(4-Chlorophenyl)piperazin-1-yl]ethyl}-(5-methyl-1-[1,6]naphthyridin-2-yl)amine;
[2-(4-Benzenesulfonylpiperazin-1-yl)ethyl]-(5-methyl[1,6]naphthyridin-2-yl)amine;
(5-Methyl[1,6]naphthyridin-2-yl-{2-[4-(3-phenylpropyl)piperazin-1-yl]ethyl}amine;
(5-Methyl[1,6]naphthyridin-2-yl)-[2-(4-phenethylpiperazin-1-yl)ethyl]amine;
[2-(4-Benzylpiperidin-1-yl)ethyl]-5,7-dimethyl[1,6]naphthyridin-2-yl)amine;
[2-(4-Benzenesulfonylpiperazin-1-yl)ethyl]-(5,7-dimethyl[1,6]naphthyridin-2-yl)amine;
[2-(4-Benzylpiperidin-1-yl)ethyl]-(5-phenyl[1,6]naphthyridin-2-yl)amine;
N,N-Dimethyl-N'-(5-methyl[1,6]naphthyridin-2-yl)ethane-1,2-diamine;
[2-(4-Benzylpiperidin-1-yl)ethyl]-(5-isopropyl[1,6]naphthyridin-2-yl)amine;
[2-(4-Benzylpiperidin-1-yl)ethyl]-(5-ethyl[1,6]naphthyridin-2-yl)amine;
[2-(4-Benzylpiperidin-1-yl)ethyl]-[1,6]naphthyridin-2-yl)amine;
[2-(4-Benzylpiperidin-1-yl)ethyl]-(7-methyl[1,6]naphthyridin-2-yl)amine;
(5-Methyl[1,6]naphthyridin-2-yl)-[2-(4-phenethylpiperidin-1-yl)ethyl]amine;
[2-(4-Benzylpiperidin-1-yl)ethyl]-(5-methoxy-7-methyl[1,6]naphthyridin-2-yl)amine;
[2-(4-Benzyloxypiperidin-1-yl)ethyl]-(5-methyl[1,6]naphthyridin-2-yl)amine;
(1-Ethylpyrrolidin-2-ylmethyl)-(5-methyl[1,6]naphthyridin-2-yl)amine;
(5-Methyl[1,6]naphthyridin-2-yl)-(2-pyrrolidin-1-ylethyl)amine;
(2-Azepan-1-ylethyl)-(5-methyl[1,6]naphthyridin-2-yl)amine;
(1-Benzylpyrrolidin-3-yl)-(5-methyl[1,6]naphthyridin-2-yl)amine;
(3-Azepan-1-ylpropyl)-(5-methyl[1,6]naphthyridin-2-yl)amine;
[3-(4-Benzylpiperidin-1-yl)propyl]-(5-methyl[1,6]naphthyridin-2-yl)amine;
(5-Methyl[1,6]naphthyridin-2-yl)-[3-(2-methylpiperidin-1-yl)propyl]amine;
(5-Methyl[1,6]naphthyridin-2-yl)-(3-piperidin-1-ylpropyl)amine;
2-(4-Benzylpiperidin-1-yl)ethyl]methyl(5-methyl[1,6]naphthyridin-2-yl)amine;
[3-(2,6-Dimethylpiperidin-1-yl)propyl]-(5-methyl[1,6]naphthyridin-2-yl)amine;
{2-[4-(4-Fluorophenoxy)piperidin-1-yl]ethyl}-(5-methyl[1,6]naphthyridin-2-yl)amine;
(5-Methyl[1,6]naphthyridin-2-yl)-{2-[4-(4-trifluoromethylphenoxy)piperidin-1-yl]ethyl}amine;
[2-(1-Benzylpiperidin-4-yl)ethyl]-(5-methyl[1,6]naphthyridin-2-yl)amine;
{1-[2-(5-Methyl[1,6]naphthyridin-2-ylamino)ethyl]piperidin-4-yl}diphenylmethanol;
1-[2-(4-Benzylpiperidin-1-yl)ethyl]-3-(5-methyl[1,6]naphthyridin-2-yl)urea;
[2-(4-Benzhydryloxypiperidin-1-yl)ethyl]-(5-methyl[1,6]naphthyridin-2-yl)amine;
{2-[4-(3,5-Dimethoxybenzyloxy)piperidin-1-yl]ethyl}-(5-methyl[1,6]naphthyridin-2-yl)amine;
(5-Methyl[1,6]naphthyridin-2-yl)-{2-[4-(5-methyl[1,6]naphthyridin-2-yl)piperazin-1-yl]ethyl}amine;
(5-Methyl[1,6]naphthyridin-2-yl)-{2-[4-(3-phenylpropyl)piperidin-1-yl]ethyl}amine;

(5-Methyl[1,6]naphthyridin-2-yl)-{2-[4-(4-trifluoromethylbenzenesulfonyl)piperazin-1-yl]ethyl}amine;
4-{4-[2-(5-Methyl[1,6]naphthyridin-2-ylamino)ethyl]piperazine-1-sulfonyl}benzonitrile;
{2-[4-(4-Fluorobenzenesulfonyl)piperazin-1-yl]ethyl}-(5-methyl[1,6]naphthyridin-2-yl)amine;
{2-[4-(4-Methoxybenzenesulfonyl)piperazin-1-yl]ethyl}-(5-methyl[1,6]naphthyridin-2-yl)amine;
{2-[4-(6-Chloropyridine-3-sulfonyl)piperazin-1-yl]ethyl}-(5-methyl[1,6]naphthyridin-2-yl)amine;
[2-(4-Methanesulfonylpiperazin-1-yl)ethyl]-(5-methyl[1,6]naphthyridin-2-yl)amine;
(5-Methyl[1,6]naphthyridin-2-yl)-[2-(4-phenylmethanesulfonylpiperazin-1-yl)ethyl]amine;
{2-[4-(4-Bromobenzenesulfonyl)piperazin-1-yl]ethyl}-(5-methyl[1,6]naphthyridin-2-yl)amine;
{2-[4-(4-Chlorobenzenesulfonyl)piperazin-1-yl]ethyl}-(5-methyl[1,6]naphthyridin-2-yl)amine;
{2-[4-(4-Methanesulfonylbenzenesulfonyl)piperazin-1-yl]ethyl}-(5-methyl[1,6]naphthyridin-2-yl)amine;
{2-[4-(4-tert-Butylbenzenesulfonyl)piperazin-1-yl]ethyl}-(5-methyl[1,6]naphthyridin-2-yl)amine;
(5-Methyl[1,6]naphthyridin-2-yl)-{2-[4-(2,4,6-trichlorobenzenesulfonyl)piperazin-1-yl]ethyl}amine;
(5-Methyl[1,6]naphthyridin-2-yl)-{2-[4-(2-trifluoromethoxybenzenesulfonyl)piperazin-1-yl]ethyl}amine;
(5-Methyl[1,6]naphthyridin-2-yl)-{2-[4-(3-trifluoromethoxybenzenesulfonyl)piperazin-1-yl]ethyl}amine;
(5-Methyl[1,6]naphthyridin-2-yl)-{2-[4-(4-trifluoromethoxybenzenesulfonyl)piperazin-1-yl]ethyl}amine;
{2-[4-(4-Fluorobenzenesulfonyl)piperidin-1-yl]ethyl}-(5-methyl[1,6]naphthyridin-2-yl)amine;
N-{1-[2-(5-Methyl[1,6]naphthyridin-2-ylamino)ethyl]piperidin-4-yl}-C-phenylmethanesulfonamide;
N-{1-[2-(5-Methyl[1,6]naphthyridin-2-ylamino)ethyl]piperidin-4-yl}-benzenesulfonamide;
N-{1-[2-(5-Methyl[1,6]naphthyridin-2-ylamino)ethyl]piperidin-4-yl}-4-trifluoromethylbenzenesulfonamide;
{2-[3-(4-Fluorobenzenesulfonyl)piperidin-1-yl]ethyl}-(5-methyl[1,6]naphthyridin-2-yl)amine;
1-[2-(5-Methyl[1,6]naphthyridin-2-ylamino)ethyl]piperidine-4-sulfonic acid benzhydrylamide;
{2-[3-(4-Fluorobenzenesulfonyl)pyrrolidin-1-yl]ethyl}-(5-methyl[1,6]naphthyridin-2-yl)amine;
{2-[4-(2,2-Diphenylethanesulfonyl)piperazin-1-yl]ethyl}-(5-methyl[1,6]naphthyridin-2-yl)amine;
{2-[4-(Diphenylmethanesulfonyl)piperazin-1-yl]ethyl}-(5-methyl[1,6]naphthyridin-2-yl)amine; and
1-{4-[2-(5-Methyl[1,6]naphthyridin-2-ylamino)ethyl]piperazin-1-yl}-3,3-diphenylpropan-1-one,
or a tautomer, prodrug, solvate, or salt thereof.

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

A. Chemical Nomenclature, Terms, and Conventions

In the groups, radicals, or moieties defined below, the number of carbon atoms is often specified preceding the group, for example, $C_1$-$C_{10}$-alkyl means an alkyl group or radical having 1 to 10 carbon atoms. The term "lower" applied to any carbon-containing group means a group containing from 1 to 8 carbon atoms, as appropriate to the group (i.e., a cyclic group must have at least 3 atoms to constitute a ring). In general, for groups comprising two or more subgroups, the last named group is the radical attachment point, for example, "alkylaryl" means a monovalent radical of the formula Alk-Ar-, while "arylalkyl" means a monovalent radical of the formula Ar-Alk- (where Alk is an alkyl group and Ar is an aryl group). Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups.

The terms "alkyl" or "alkyl group" mean a branched or straight-chain saturated aliphatic hydrocarbon monovalent radical. This term is exemplified by groups such as methyl, ethyl, n-propyl, 1-methylethyl (isopropyl), n-butyl, n-pentyl, 1,1-dimethylethyl (tert-butyl), and the like. It may be abbreviated "Alk".

The terms "alkenyl" or "alkenyl group" mean a branched or straight-chain aliphatic hydrocarbon monovalent radical containing at least one carbon-carbon double bond. This term is exemplified by groups such as ethenyl, propenyl, n-butenyl, isobutenyl, 3-methylbut-2-enyl, n-pentenyl, heptenyl, octenyl, decenyl, and the like.

The terms "alkynyl" or "alkynyl group" mean a branched or straight-chain aliphatic hydrocarbon monovalent radical containing at least one carbon-carbon triple bond. This term is exemplified by groups such as ethynyl, propynyl, n-butynyl, 2-butynyl, 3-methylbutynyl, n-pentynyl, heptynyl, octynyl, decynyl, and the like.

The terms "alkylene" or "alkylene group" mean a branched or straight-chain saturated aliphatic hydrocarbon divalent radical having the specified number of carbon atoms. This term is exemplified by groups such as methylene, ethylene, propylene, n-butylene, and the like, and may alternatively and equivalently be denoted herein as -(alkyl)-.

The terms "alkenylene" or "alkenylene group" mean a branched or straight-chain aliphatic hydrocarbon divalent radical having the specified number of carbon atoms and at least one carbon-carbon double bond. This term is exemplified by groups such as ethenylene, propenylene, n-butenylene, and the like, and may alternatively and equivalently be denoted herein as -(alkylenyl)-.

The terms "alkynylene" or "alkynylene group" mean a branched or straight-chain aliphatic hydrocarbon divalent radical containing at least one carbon-carbon triple bond. This term is exemplified by groups such as ethynylene, propynylene, n-butynylene, 2-butynylene, 3-methylbutynylene, n-pentynylene, heptynylene, octynylene, decynylene, and the like, and may alternatively and equivalently be denoted herein as -(alkynyl)-.

The terms "alkoxy" or "alkoxy group" mean a monovalent radical of the formula AlkO—, where Alk is an alkyl group. This term is exemplified by groups such as methoxy, ethoxy, propoxy, isopropoxy, butoxy, sec-butoxy, tert-butoxy, pentoxy, and the like.

The terms "amino" or "amino group" mean an —$NH_2$ group.

The terms "alkylamino" or "alkylamino group" mean a monovalent radical of the formula (Alk)NH—, where Alk is alkyl. Exemplary alkylamino groups include methylamino, ethylamino, propylamino, butylamino, tert-butylamino, and the like.

The terms "dialkylamino" or "dialkylamino group" mean a monovalent radical of the formula (Alk)(Alk)N—, where each Alk is independently alkyl. Exemplary dialkylamino groups include dimethylamino, methylethylamino, diethylamino, dipropylamino, ethylpropylamino, and the like.

The terms "substituted amino" or "substituted amino group" mean a monovalent radical of the formula —$NR_2$, where each R is independently a substituent selected from hydrogen or the specified substituents (but where both $R^s$ cannot be hydrogen). Exemplary substituents include alkyl, alkanoyl, aryl, arylalkyl, cycloalkyl, heterocyclyl, heteroaryl, heteroarylalkyl, and the like.

The terms "halogen" or "halogen group" mean a fluoro, chloro, bromo, or iodo group.

The terms "aryl" or "aryl group" mean an aromatic carbocyclic monovalent or divalent radical of from 6 to 14 carbon atoms having a single ring (e.g., phenyl or phenylene) or multiple condensed rings (e.g., naphthyl or anthranyl). The term "aryl" also encompasses a benzhydryl moiety. Unless otherwise specified, the aryl ring may be attached at any suitable carbon atom which results in a stable structure and, if substituted, may be substituted at any suitable carbon atom which results in a stable structure. Exemplary aryl groups include phenyl, naphthyl, anthryl, phenanthryl, indanyl, indenyl, biphenyl, benzhydryl and the like. It may be abbreviated "Ar".

The terms "heteroaryl" or "heteroaryl group" mean a stable aromatic 5- to 14-membered, monocyclic or polycyclic monovalent or divalent radical which may comprise one or more fused or bridged ring(s), preferably a 5- to 7-membered monocyclic or 7- to 10-membered bicyclic radical, having from one to four heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heteroaryl ring may be attached at any suitable heteroatom or carbon atom which results in a stable structure and, if substituted, may be substituted at any suitable heteroatom or carbon atom which results in a stable structure. Exemplary and preferred heteroaryls include furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, triazinyl, indolizinyl, azaindolizinyl, indolyl, azaindolyl, diazaindolyl, dihydroindolyl, dihydroazaindoyl, isoindolyl, azaisoindolyl, benzofuranyl, furanopyridinyl, furanopyrimidinyl, furanopyrazinyl, furanopyridazinyl, dihydrobenzofuranyl, dihydrofuranopyridinyl, dihydrofuranopyrimidinyl, benzodioxolanyl, benzothienyl, thienopyridinyl, thienopyrimidinyl, thienopyrazinyl, thienopyridazinyl, dihydrobenzothienyl, dihydrothienopyridinyl, dihydrothienopyrimidinyl, indazolyl, azaindazolyl, diazaindazolyl, benzimidazolyl, imidazopyridinyl, benzthiazolyl, thiazolopyridinyl, thiazolopyrimidinyl, benzoxazolyl, oxazolopyridinyl, oxazolopyrimidinyl, benzisoxazolyl, purinyl, chromanyl, azachromanyl, quinolizinyl, quinolinyl, dihydroquinolinyl, tetrahydroquinolinyl, isoquinolinyl, dihydroisoquinolinyl, tetrahydroisoquinolinyl, cinnolinyl, azacinnolinyl, phthalazinyl, azaphthalazinyl, quinazolinyl, azaquinazolinyl, quinoxalinyl, azaquinoxalinyl, naphthyridinyl, dihydronaphthyridinyl, tetrahydronaphthyridinyl, pteridinyl, carbazolyl, acridinyl, phenazinyl, phenothiazinyl, and phenoxazinyl, and the like.

The terms "heterocycle", "heterocycle group", "heterocyclyl", or "heterocyclyl group" mean a stable non-aromatic 5- to 14-membered monocyclic or polycyclic, monovalent or divalent, ring which may comprise one or more fused or bridged ring(s), preferably a 5- to 7-membered monocyclic or 7- to 10-membered bicyclic ring, having from one to three heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heterocyclyl ring may be attached at any suitable heteroatom or carbon atom which results in a stable structure and, if substituted, may be substituted at any suitable heteroatom or carbon atom which results in a stable structure. Exemplary and preferred heterocycles include pyrrolinyl, pyrrolidinyl, pyrazolinyl, pyrazolidinyl, piperidinyl, morpholinyl, thiomorpholinyl, piperazinyl, tetrahydropyranyl, tetrahydrothiopyranyl, tetrahydrofuranyl, hexahydropyrimidinyl, hexahydropyridazinyl, and the like.

The term "compounds of the invention" and equivalent expressions are meant to embrace compounds of Formula (I) as herein described, including the tautomers, the prodrugs, the salts, particularly the pharmaceutically acceptable salts, and the solvates and hydrates thereof, where the context so permits. In general and preferably, the compounds of the invention and the formulas designating the compounds of the invention are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits.

The terms "optional" or "optionally" mean that the subsequently described event or circumstances may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution.

The terms "stable compound" or "stable structure" mean a compound that is sufficiently robust to survive isolation to a useful degree of purity from a reaction mixture, and formulation into an efficacious therapeutic or diagnostic agent. For example, a compound which would have a "dangling valency" or is a carbanion is not a compound contemplated by the invention.

The term "substituted" means that any one or more hydrogens on an atom of a group or moiety, whether specifically designated or not, is replaced with a selection from the indicated group of substituents, provided that the atom's normal valency is not exceeded and that the substitution results in a stable compound. If a bond to a substituent is shown to cross the bond connecting two atoms in a ring, then such substituent may be bonded to any atom on the ring. When a substituent is listed without indicating the atom via which such substituent is bonded to the rest of the compound, then such substituent may be bonded via any atom in such substituent. For example, when the substituent is piperazinyl, piperidinyl, or tetrazolyl, unless specified otherwise, such piperazinyl, piperidinyl, or tetrazolyl group may be bonded to the rest of the compound of the invention via any atom in such piperazinyl, piperidinyl, or tetrazolyl group. Generally, when any substituent or group occurs more than one time in any constituent or compound, its definition on each occurrence is independent of its definition at every other occurrence. Thus, for example, if a group is shown to be substituted with 0 to 2 $R^5$, then such group is optionally substituted with up to two $R^5$ groups and $R^5$ at each occurrence is selected independently from the defined list of possible $R^5$. Such combinations of substituents and/or variables, however, are permissible only if such combinations result in stable compounds.

In a specific embodiment, the term "about" or "approximately" means within 20%, preferably within 10%, and more preferably within 5% of a given value or range.

The yield of each of the reactions described herein is expressed as a percentage of the theoretical yield.

B. Salt, Prodrug, Derivative, and Solvate Terms and Conventions

The term "prodrug" means a covalently-bonded derivative or carrier of the parent compound or active drug substance which undergoes at least some biotransformation prior to exhibiting its pharmacological effect(s). In general, such prodrugs have metabolically cleavable groups and are rapidly transformed in vivo to yield the parent compound, for example, by hydrolysis in blood, and generally include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in *A Textbook of Drug Design and Development*, Krogsgaard-Larsen and H. Bundgaard (eds.), Gordon & Breach, 1991, particularly Chapter 5: "Design and Applications of Prodrugs"; *Design of Prodrugs*, H. Bundgaard (ed.), Elsevier, 1985; *Prodrugs: Topical and Ocular Drug Delivery*, K. B. Sloan (ed.), Marcel Dekker, 1998; *Methods in Enzymology*, K. Widder et al. (eds.), Vol. 42, Academic Press, 1985, particularly pp. 309-396; *Burger's Medicinal Chemistry and Drug Discovery*, 5th Ed., M. Wolff (ed.), John Wiley & Sons, 1995, particularly Vol. 1 and pp. 172-178 and pp. 949-982; *Pro-Drugs as Novel Delivery Systems*, T. Higuchi and V. Stella (eds.), Am. Chem. Soc., 1975; *Bioreversible Carriers in Drug Design*, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The term "salt" means an ionic form of the parent compound or the product of the reaction between the parent compound with a suitable acid or base to make the acid salt or base salt of the parent compound. Salts of the compounds of the present invention can be synthesized from the parent compounds which contain a basic or acidic moiety by conventional chemical methods. Generally, the salts are prepared by reacting the free base or acid parent compound with stoichiometric amounts or with an excess of the desired salt-forming inorganic or organic acid or base in a suitable solvent or various combinations of solvents.

The term "pharmaceutically acceptable salt" means a salt of a compound of the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. As the compounds of the present invention are useful in both free base and salt form, in practice, the use of the salt form amounts to use of the base form. Lists of suitable salts are found in, e.g., S. M. Birge et al., J. Pharm. Sci., 1977, 66, pp. 1-19, which is hereby incorporated by reference in its entirety.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

The term "solvate" means a physical association of a compound with one or more solvent molecules or a complex of variable stoichiometry formed by a solute (for example, a compound of Formula (I)) and a solvent, for example, water, ethanol, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, the solvents selected do not interfere with the biological activity of the solute. Solvates encompasses both solution-phase and isolatable solvates. Representative solvates include hydrates, ethanolates, methanolates, and the like.

The term "hydrate" means a solvate wherein the solvent molecule(s) is/are $H_2O$.

The compounds of the present invention as discussed below include the free base or acid thereof, their salts, solvates, and prodrugs and may include oxidized sulfur atoms or quaternized nitrogen atoms in their structure, although not explicitly stated or shown, particularly the pharmaceutically acceptable forms thereof. Such forms, particularly the pharmaceutically acceptable forms, are intended to be embraced by the appended claims.

C. Isomer Terms and Conventions

The term "isomers" means compounds having the same number and kind of atoms, and hence the same molecular weight, but differing with respect to the arrangement or configuration of the atoms in space. The term includes stereoisomers and geometric isomers.

The terms "stereoisomer" or "optical isomer" mean a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of the invention which may give rise to stereoisomerism, the invention contemplates stereoisomers and mixtures thereof. The compounds of the invention and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures. As discussed in more detail below, individual stereoisomers of compounds are prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

The term "enantiomers" means a pair of stereoisomers that are non-superimposable minor images of each other.

The terms "diastereoisomers" or "diastereomers" mean optical isomers which are not minor images of each other.

The terms "racemic mixture" or "racemate" mean a mixture containing equal parts of individual enantiomers.

The term "non-racemic mixture" means a mixture containing unequal parts of individual enantiomers.

The term "geometrical isomer" means a stable isomer which results from restricted freedom of rotation about double bonds (e.g., cis-2-butene and trans-2-butene) or in a cyclic structure (e.g., cis-1,3-dichlorocyclobutane and trans-1,3-dichlorocyclobutane). Because carbon-carbon double (olefinic) bonds, C=N double bonds, cyclic structures, and the like may be present in the compounds of the invention, the invention contemplates each of the various stable geometric isomers and mixtures thereof resulting from the arrangement of substituents around these double bonds and in these cyclic structures. The substituents and the isomers are designated using the cis/trans convention or using the E or Z system, wherein the term "E" means higher order substituents on opposite sides of the double bond, and the term "Z" means higher order substituents on the same side of the double bond. A thorough discussion of E and Z isomerism is provided in J. March, *Advanced Organic Chemistry: Reactions, Mechanisms, and Structure*, 4th ed., John Wiley & Sons, 1992, which is hereby incorporated by reference in its entirety. Several of the following examples represent single E isomers, single Z isomers, and mixtures of E/Z isomers. Determination of the E and Z isomers can be done by analytical methods such as X-ray crystallography, $^1$H NMR, and $^{13}$C NMR.

Some of the compounds of the invention can exist in more than one tautomeric form. As mentioned above, the compounds of the invention include all such tautomers.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the invention from this disclosure and the knowledge of the prior art.

Thus, although the racemic form of drug may be used, it is often less effective than administering an equal amount of enantiomerically pure drug; indeed, in some cases, one enantiomer may be pharmacologically inactive and would merely serve as a simple diluent. For example, although ibuprofen had been previously administered as a racemate, it has been shown that only the S-isomer of ibuprofen is effective as an anti-inflammatory agent (in the case of ibuprofen, however, although the R-isomer is inactive, it is converted in vivo to the S-isomer, thus, the rapidity of action of the racemic form of the drug is less than that of the pure S-isomer). Furthermore, the pharmacological activities of enantiomers may have distinct biological activity. For example, S-penicillamine is a therapeutic agent for chronic arthritis, while R-penicillamine is toxic. Indeed, some purified enantiomers have advantages over the racemates, as it has been reported that purified individual isomers have faster transdermal penetration rates compared to the racemic mixture. See U.S. Pat. Nos. 5,114,946 and 4,818,541.

Thus, if one enantiomer is pharmacologically more active, less toxic, or has a preferred disposition in the body than the other enantiomer, it would be therapeutically more beneficial to administer that enantiomer preferentially. In this way, the patient undergoing treatment would be exposed to a lower total dose of the drug and to a lower dose of an enantiomer that is possibly toxic or an inhibitor of the other enantiomer.

Preparation of Pure Enantiomers or Mixtures of Desired Enantiomeric Excess (Ee) or enantiomeric purity are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in *Chiral Separation Techniques: A Practical Approach* (2nd Ed.), G. Subramanian (ed.), Wiley-VCH, 2000; T. E. Beesley and R. P. W. Scott, *Chiral Chromatography*, John Wiley & Sons, 1999; and Satinder Ahuja, *Chiral Separations by Chromatography*, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

In general, all tautomeric forms and isomeric forms and mixtures, whether individual geometric isomers or stereoisomers or racemic or non-racemic mixtures, of a chemical structure or compound is intended, unless the specific stereochemistry or isomeric form is specifically indicated in the compound name or structure.

D. Pharmaceutical Administration and Diagnostic and Treatment Terms and Conventions The term "patient" includes both human and non-human mammals.

The term "effective amount" means an amount of a compound according to the invention which, in the context of which it is administered or used, is sufficient to achieve the desired effect or result. Depending on the context, the term effective amount may include or be synonymous with a pharmaceutically effective amount or a diagnostically effective amount.

The terms "pharmaceutically effective amount" or "therapeutically effective amount" means an amount of a compound according to the invention which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound of according to the invention which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the invention, and the age, body weight, general health, sex, and diet of the patient. Such a therapeutically effective amount can be determined routinely by one of ordinary skill in the art having regard to their own knowledge, the prior art, and this disclosure.

The term "diagnostically effective amount" means an amount of a compound according to the invention which, when used in a diagnostic method, apparatus, or assay, is sufficient to achieve the desired diagnostic effect or the desired biological activity necessary for the diagnostic method, apparatus, or assay. Such an amount would be sufficient to elicit the biological or medical response in a diagnostic method, apparatus, or assay, which may include a biological or medical response in a patient or in a in vitro or in vivo tissue or system, that is sought by a researcher or clinician. The amount of a compound according to the invention which constitutes a diagnostically effective amount will vary depending on such factors as the compound and its biological activity, the diagnostic method, apparatus, or assay used, the composition used for administration, the time of administration, the route of administration, the rate of excretion of the compound, the duration of administration, drugs and other compounds used in combination with or coincidentally with the compounds of the invention, and, if a patient is the subject of the diagnostic administration, the age, body weight, general health, sex, and diet of the patient. Such a diagnostically effective amount can be determined routinely by one of ordinary skill in the art having regard to their own knowledge, the prior art, and this disclosure.

The term "antagonist" in the context of describing compounds according to the invention means a compound that directly or indirectly inhibits or suppresses U-II activity resulting from its interaction with the U-II receptor. As such, antagonists include partial antagonists and full antagonists.

The term "full antagonist" in the context of describing compounds according to the invention means a compound that evokes the maximal inhibitory response from the U-II/U-II receptor interaction, even when there are spare (unoccupied) U-II receptors present.

The term "partial antagonist" in the context of describing compounds according to the invention means a compound that is unable to evoke the maximal inhibitory response from the U-II/U-II receptor interaction, even at concentrations sufficient to saturate the U-II receptors present.

The terms "treating" or "treatment" mean the treatment of a disease-state in a patient, and include:
(i) preventing the disease-state from occurring in a patient, in particular, when such patient is genetically or otherwise predisposed to the disease-state but has not yet been diagnosed as having it;
(ii) inhibiting or ameliorating the disease-state in a patient, i.e., arresting or slowing its development; or
(iii) relieving the disease-state in a patient, i.e., causing regression or cure of the disease-state.

General Synthetic Methods

The invention also provides processes for making compounds of Formula (I). In all schemes, unless specified otherwise, $R^1$ to $R^7$ in the formulas below shall have the meaning of $R^1$ to $R^7$ in the Formula (I) of the invention described herein above. Intermediates used in the preparation of compounds of the invention are either commercially available or readily prepared by methods known to those skilled in the art.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Experimental Examples section. Typically, reaction progress may be monitored by thin layer chromatography (TLC), if desired, and intermediates and products may be purified by chromatography on silica gel, HPLC and/or by recrystallization.

Compounds of Formula (I) may be prepared by the method outlined in Scheme I.

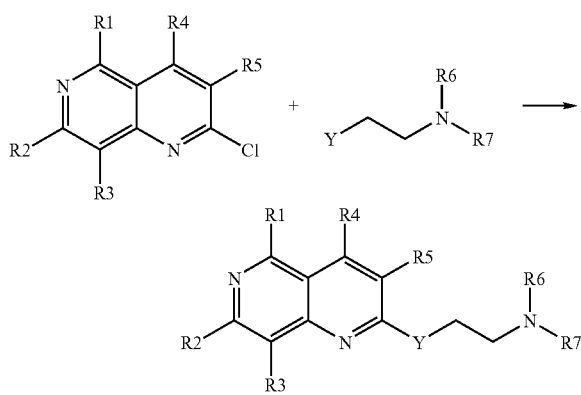

As illustrated in Scheme I, a 2-chloro-1,6-naphthyridine is treated with an amine containing a nucleophilic group YH, in the presence of a suitable base, to provide the desired compound of formula (I) (Y is —NH—, —O—, or —S—. For example, to prepare compounds of formula (I) where Y is —NH—, the 2-chloro-1,6-naphthyridine may be treated with the desired diamine (Y is —NH$_2$) in the presence of 2.0 equivalents of sodium carbonate (Na$_2$CO$_3$), under microwave conditions, typically 125° C. for 30 minutes, to yield the desired compound of formula (I) having Y is —NH—. Alternatively, the aryl chloride could be coupled to the amines of interest in the presence of a suitable amine base such as diisopropylethylamine in a suitable solvent such as acetonitrile and heating or in the presence of a Pd catalyst, appropriate base, and conventional thermal heating as described in the Synthetic Examples section. The various substituted 1,6-naphthyridine chlorides may be prepared as described in the literature (Singh et al., Synthesis, 1991, 10, 894; Baldev et al., J. Heterocyclic Chem., 1990, 27, 2085; Hawes et al., J. Heterocyclic Chem., 1974, 151; J. Med. Chem. 1973, 16, 7, 849) and described in detail for the 5-methyl naphthyridine in Example 1 below. The various amine components (N-ethylamino-4-benzyl piperidine and analogs thereof) may be prepared following literature procedures (J. Med. Chem., 1990, 33, 2970). Compounds of formula (I) where Y is —O— or —S— may be synthesized by deprotonation of the corresponding alcohol precursors (purchased or synthesized through standard synthetic routes) with NaH followed by treatment with the naphthyridine chloride. Compounds of formula (I) where Y is —NHC(O)NH— or —NHC(O)— may be prepared by treatment of the aryl chloride with NH$_4$OH to produce the corresponding aryl amine, followed by further functionalization of the amine by methods known in the art and illustrated in the Synthetic Examples section.

In order that this invention by more fully understood, the following examples are set forth. These examples are for the purpose of illustrating embodiments of this invention, and are not to be construed as limiting the scope of the invention in any way since, as recognized by one skilled in the art, particular reagents or conditions could be modified as needed for individual compounds. Starting materials used are either commercially available or easily prepared from commercially available materials by those skilled in the art.

Synthetic Examples

Example 1

Synthesis of 2-chloro-5-methyl[1,6]naphthyridine intermediate (1)

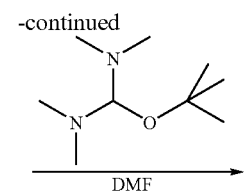

-continued

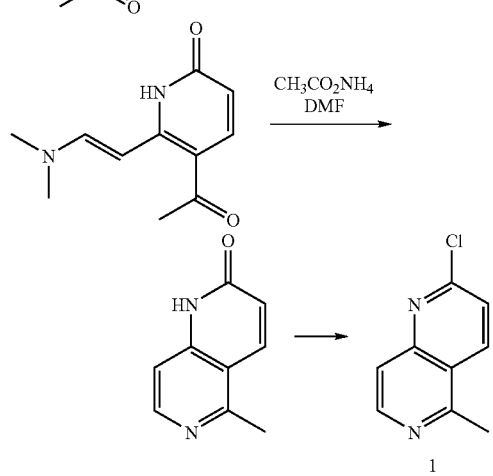

To a stirred solution of enamine (0.1 mol) and DMF (75 mL) was added methyl propiolate (0.11 mol) over 15 minutes. The resulting solution was stirred at room temperature for 3.5 hours and then heated to reflux for 24 hours. After cooling to room temperature, the light tan solid was filtered off to afford the desired pyridinone (47%).

A mixture of pyridinone (0.26 mol) and Bredereck's reagent (0.3 mol) in dioxane was heated to reflux while stirring for 2.5 hours. A bright yellow solid crystallized during the reaction. The reaction mixture was cooled to room temperature and the product was collected by filtration to yield desired product (96%).

A mixture of the pyridinone enamine (0.18 mole), ammonium acetate (0.35 mole), and DMF (250 mL) was heated to reflux with stirring for 2 hours and then cooled to room temperature. The light yellow solid was collected, washed with ethanol, and dried to afford the desired naphthyridinone (98%).

To a stirred solution of naphthyridinone (32 g, 0.2 mol) and POCl$_3$ (500 mL) was added PCl$_5$ (42 g, 0.2 mol). The resulting mixture was heated to reflux for 7 hours and then most of the POCl$_3$ was removed under reduced pressure. The dark residue was taken up in a slurry of CHCl$_3$ (500 mL) and poured slowly into a vigorously stirred mixture of potassium carbonate (K$_2$CO$_3$; 138 g, 1 mol) and water (300 mL) cooled in an ice bath. The temperature was kept below 10° C. by adding ice to the reaction mixture and more potassium carbonate was added to keep the reaction mixture on the basic side. The organic layer was separated and dried over magnesium sulfate (MgSO$_4$). Removal of CHCl$_3$ gave 37.8 g of a purple solid which was purified by column chromatography (SiO$_2$ 600 g, 5% MeOH in Et$_2$O). Recrystallization from Et$_2$O-hexanes gave compound 1 (27.5 g, 77%) as a pale yellow solid, mp=98° C.-100° C.

The various 5-substituted naphthyridine-2-chlorides (ethyl, isopropyl, phenyl) used for other analogs were synthesized following a similar synthetic method using the appropriate starting materials. The 3-substituted napthyridines were synthesized from known intermediates (Hawes et al., J. Heterocyclic Chem., 1974, 151) using a similar method.

Example 2

Synthesis of 2-chloro-5,7-dimethyl[1,6]naphthyridine intermediate (2)

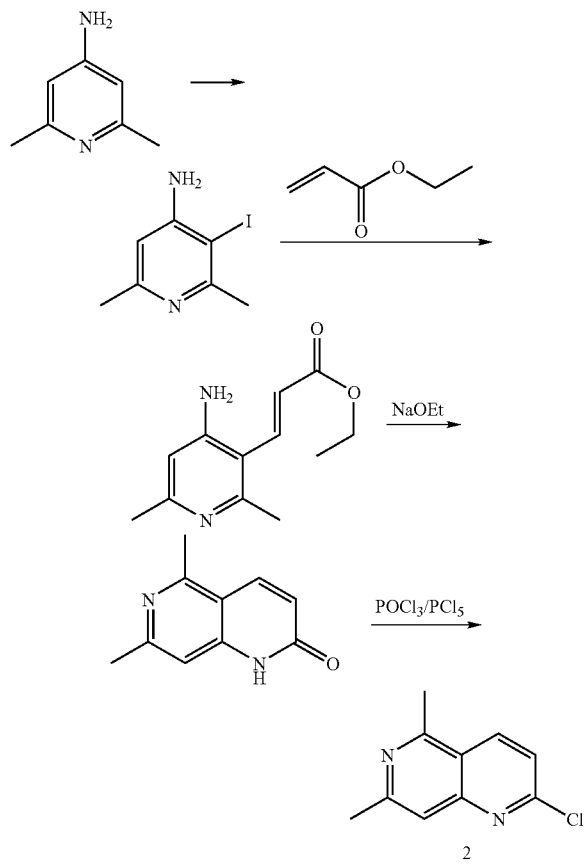

4-Amino-2,6-dimethylpyridine (2.29 g, 18.7 mmol) was added to a solution of iodine (4.78 g, 18.8 mmol) and [bis(trifluoroacetoxy)iodo]benzene (8.1 g, 18.8 mmol) in dichloromethane (100 mL) and MeOH (30 mL). The mixture was stirred at room temperature for 16 hours. The reaction was quenched by addition of a mixture of saturated sodium metabisulphite solution (70 mL) and saturated sodium carbonate solution (300 mL). The organic phase was separated, washed with brine, and dried over sodium sulfate ($Na_2SO_4$). The solvent was removed and the product was purified by silica gel chromatography eluting with 30:1 dichloromethane:MeOH to afford the desired product (998 mg, 21.2%).

A stirred mixture of the iodopyridine (998 mg, 3.98 mmol), ethyl acrylate (1.04 mL, 9.57 mmol), Pd(OAc)$_2$ (22.5 mg, 0.1 mmol)), tri(2-methylphenyl)phosphine (22.5 mg, 0.074 mmol), and triethylamine (0.66 mL, 4.8 mmol) in DMF (10 mL) was heated at 130° C. for 16 hours. The solvent was removed and the product was purified by silica gel chromatography eluting with 30:1 dichloromethane:MeOH to afford the desired alkylated pyridine intermediate (494 mg, 56.3%).

To a stirred solution of alkylated pyridine intermediate above (494 mg, 2.24 mmol) in EtOH (10 mL) was added a 21% solution of NaOEt in EtOH (1.57 mL, 20.0 mmol). It was heated at reflux for 3 hours. The solvent was removed, and the residue was diluted in water (10 mL) and neutralized to pH=7 by addition of HCl (6 N). The precipitates were isolated by filtration to afford the 5,7-dimethylnaphthyridinone intermediate (156 mg, 39.9%).

To a stirred mixture of the 5,7-dimethylnaphthyridinone intermediate above (183 mg, 1.05 mmol) in acetonitrile (10 mL) was added POCl$_3$ (9.96 mL, 105 mmol). The mixture was heated at reflux for 4 hours. The solvent was removed and the residue was taken up in ethyl acetate. Ice was added to quench the remaining POCl$_3$. Sodium carbonate was added to adjust the pH to ~10. The organic phase was separated, washed with brine, and dried with sodium sulfate. The solvent was removed to afford compound 2 (203 mg, 90% purity by NMR, 90.3%). $^1$H NMR (CD$_3$OD, 400 MHz) δ 8.68 (d, 1H, J=7.5 Hz), 7.60-7.68 (m, 2H), 3.00 (s, 3H), 2.70 (s, 3H). LCMS (EI) m/z 193 (M+1).

The 7-substituted- and 5-OMe-7-Me-substituted naphthyridine chlorides were prepared as previously described (Singh et al., Synthesis, 1991, 10, 894).

Example 3

Synthesis of [2-(4-benzylpiperidin-1-yl)ethyl]-(5-methyl[1,6]naphthyridin-2-yl)amine (3)

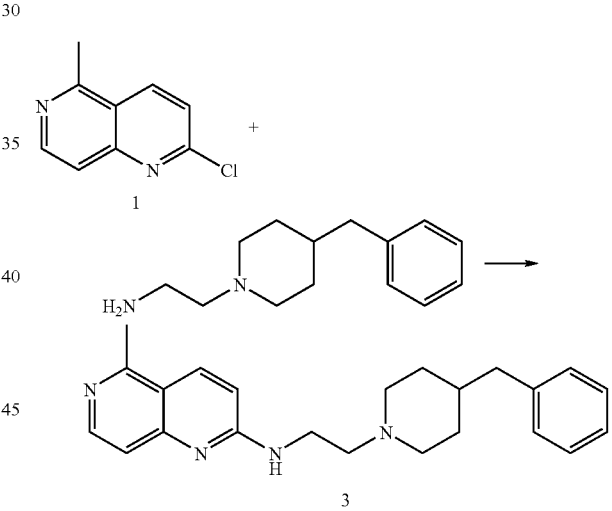

Method A

A stirred mixture of compound 1 (300.00 mg, 1.68 mmol), N-ethylamino-4-benzyl piperidine (436.68 mg, 2.00 mmol), Pd(OAc)$_2$ (22.45 mg, 0.10 mmol), 2,2'-bis(diphenylphosphino)-1-1'-binaphthyl (BINAP) (62.27 mg, 0.10 mmol), and sodium tert-butoxide (225.86 mg, 2.35 mmol) in toluene (10 mL) was heated at 80° C. under argon overnight. The reaction mixture was diluted with dichloromethane, washed with brine, dried with sodium sulfate, and purification by chromatography on silica gel (MeOH/dichloromethane=1:10) afforded compound 3 (110.00 mg, 18.2%). $^1$H NMR (CDCl$_3$, 400 MHz) δ 8.38 (1H, d, J=4.82 Hz), 8.00 (1H, d, J=9.64 Hz), 7.12-7.37 (6H, m), 6.70 (1H, d, J=9.40 Hz), 5.75-5.85 (1H, m), 3.52-3.77 (2H, m), 2.90-3.00 (2H, m), 2.81 (3H, s), 2.65 (2H, t, J=6.06 Hz), 2.55 (2H, d, 6.10 Hz), 1.93-2.06 (2H, m), 1.50-1.73 (3H, m), 1.25-1.42 (2H, m). LCMS (EI) m/z 361 (M+1).

Method B

Alternatively, compound 3 was prepared by charging a microwave vial with compound 1 (207 mg, 1.16 mmol), potassium carbonate (479 mg, 3.48 mmol), N-ethylamino-4-benzyl piperidine (379 mg, 1.74 mmol), and water (3 mL). The vial was sealed and heated under microwave irradiation at 100° C. for 30 minutes. The mixture was diluted with water and extracted with EtOAc. The organic layer was dried and evaporated. The residue was purified by chromatography on silica gel (MeOH/dichloromethane=1/10) to afford compound 3 (241 mg, 58.4%).

Example 4

Synthesis of (5-Methyl[1,6]naphthyridin-2-yl)-(2-piperidin-1-ylethyl)amine (4)

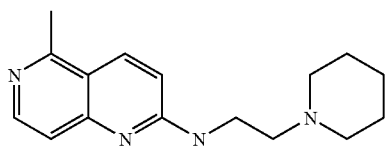

4

Compound 4 was prepared using the procedure described in Example 3, Method A. $^1$H NMR (CDCl$_3$, 400 MHz) δ 8.35 (d, 1H, J=5 Hz), 8.0 (d, 1H, J=8 Hz), 7.33 (d, 1H, J=5 Hz), 6.70 (d, 1H, J=8 Hz), 5.85-5.95 (m, 1H), 3.55-3.65 (m, 1H), 2.80 (s, 3H), 2.55-2.65 (m, 2H), 2.30-2.50 (m, 4H), 1.55-1.70 (m, 4H), 1.40-1.52 (m, 2H). LCMS (EI) m/z 271 (M+1).

Example 5

Synthesis of 1-[2-(5-Methyl[1,6]naphthyridin-2-ylamino)ethyl]piperidin-4-ol (5)

5

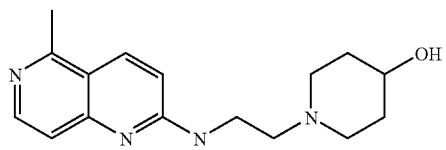

Compound 5 was prepared as described for compound 3, Method A. $^1$H NMR (CD$_3$OD, 400 MHz) δ 8.42 (d, 1H, J=7.5 Hz), 8.35 (d, 1H, J=5.5 Hz), 7.53 (d, 1H, J=7.5 Hz), 7.05 (d, 1H, J=5.5 Hz), 5.30-5.40 (m, 1H), 2.75-2.88 (m, 7H), 2.52 (t, 2H), 2.38-2.48 (m, 2H), 2.08-2.20 (m, 2H), 1.82-1.95 (m, 2H).

Example 6

Synthesis of 4-Benzyl-1-[2-(5-methyl[1,6]naphthyridin-2-ylamino)ethyl]piperidin-4-ol (6)

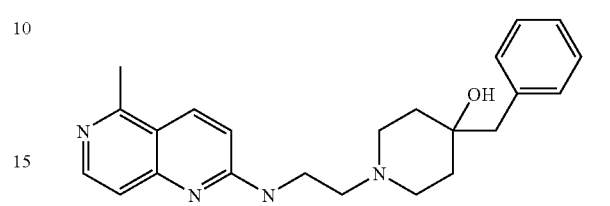

6

Compound 6 was prepared as described for compound 3, Method A, except that it was purified by prep-HPLC and was isolated as TFA salt. $^1$H NMR (CD$_3$OD, 400 MHz) δ 8.35 (d, 1H, J=7.5 Hz), 8.30 (d, 1H, J=5.3 Hz), 7.65 (d, 1H, J=7.5 Hz), 7.15-7.35 (m, 5H), 7.09 (d, 1H, J=7.5 Hz), 4.0-4.09 (m, 2H), 3.60-3.68 (m, 2H), 3.42-3.50.9m, 2H), 3.28-3.38 (m, 2H), 2.99 (s, 3H), 2.83 (s, 2H), 1.70-1.98 (m, 4H). LCMS (EI) m/z 377 (M+1).

Example 7

Synthesis of 4-[2-(5-Methyl[1,6]naphthyridin-2-ylamino)ethyl]piperazine-1-carboxylic acid tent-butyl ester (7)

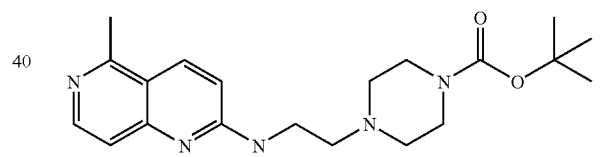

7

Compound 7 was prepared as described for compound 3, Method A. $^1$H NMR (CDCl$_3$, 400 MHz) δ 8.38 (d, 1H, 5.5 Hz), 8.05 (d, 1H, J=7.5 Hz), 7.36 (d, 1H, J=7.5 Hz), 6.68 (d, 1H, J=5.5 Hz), 5.50-5.65 (m, 1H), 3.55-3.65 (m, 2H), 3.40-3.50 (m, 4H), 2.80 (s, 3H), 2.60-2.70 (m, 2H), 2.40-2.50 (m, 2H), 1.48 (s, 9H). LCMS (EI) m/z 272 (M-tBu+1).

The following compounds were made using procedures analogous to those described in Example 3:

[2-(4-Benzylpiperidin-1-yl)ethyl]-(5-phenyl[1,6]naphthyridin-2-yl)amine;

N,N-Dimethyl-N'-(5-methyl[1,6]naphthyridin-2-yl)ethane-1,2-diamine;

[2-(4-Benzylpiperidin-1-yl)ethyl]-(5-isopropyl[1,6]naphthyridin-2-yl)amine;

[2-(4-Benzylpiperidin-1-yl)ethyl]-(5-ethyl[1,6]naphthyridin-2-yl)amine;

[2-(4-Benzylpiperidin-1-yl)ethyl]-[1,6]naphthyridin-2-yl)amine;

[2-(4-Benzylpiperidin-1-yl)ethyl]-(7-methyl[1,6]naphthyridin-2-yl)amine;

(5-Methyl[1,6]naphthyridin-2-yl)-[2-(4-phenethylpiperidin-1-yl)ethyl]amine;
Benzyl(5-methyl[1,6]naphthyridin-2-yl)amine;
[2-(4-Benzylpiperidin-1-yl)ethyl]-(5-methoxy-7-methyl[1,6]naphthyridin-2-yl)amine;
[2-(4-Benzyloxypiperidin-1-yl)ethyl]-(5-methyl[1,6]naphthyridin-2-yl)amine;
(5-Methyl[1,6]naphthyridin-2-yl)-(3-morpholin-4-ylpropyl)amine;
((S)-1-Benzylpyrrolidin-3-yl)-(5-methyl[1,6]naphthyridin-2-yl)amine;
2,2,N,N-Tetramethyl-N'-(5-methyl[1,6]naphthyridin-2-yl)propane-1,3-diamine;
N,N-Dimethyl-N'-(5-methyl[1,6]naphthyridin-2-yl)propane-1,3-diamine;
(1-Ethylpyrrolidin-2-ylmethyl)-(5-methyl[1,6]naphthyridin-2-yl)amine;
(5-Methyl[1,6]naphthyridin-2-yl)-(2-pyrrolidin-1-ylethyl)amine;
1-[3-(5-Methyl[1,6]naphthyridin-2-ylamino)propyl]pyrrolidin-2-one;
N,N-Diisopropyl-N'-(5-methyl[1,6]naphthyridin-2-yl)ethane-1,2-diamine;
1-[2-(5-Methyl[1,6]naphthyridin-2-ylamino)ethyl]pyrrolidin-2-one;
(2-Azepan-1-ylethyl)-(5-methyl[1,6]naphthyridin-2-yl)amine;
2-[2-(4-Benzylpiperidin-1-yl)ethylamino]-[1,6]naphthyridine-3-carbonitrile;
(5-Benzylpyrrolidin-2-yl)-(5-methyl[1,6]naphthyridin-2-yl)amine;
(5-Methyl[1,6]naphthyridin-2-yl)-[2-(2-methylpyrrolidin-1-yl)ethyl]amine;
(3-Azepan-1-ylpropyl)-(5-methyl[1,6]naphthyridin-2-yl)amine;
[3-(4-Benzylpiperidin-1-yl)propyl]-(5-methyl[1,6]naphthyridin-2-yl)amine;
(5-Methyl[1,6]naphthyridin-2-yl)-[3-(2-methylpiperidin-1-yl)propyl]amine;
(5-Methyl[1,6]naphthyridin-2-yl)-(3-piperidin-1-ylpropyl)amine;
2-(4-Benzylpiperidin-1-yl)ethyl]methyl-(5-methyl[1,6]naphthyridin-2-yl)amine;
[3-(2,6-Dimethylpiperidin-1-yl)propyl]-(5-methyl[1,6]naphthyridin-2-yl)amine;
2-(4-Benzylpiperidin-1-yl)-N-(5-methyl[1,6]naphthyridin-2-yl)acetamide;
{2-[4-(4-Fluorophenoxy)piperidin-1-yl]ethyl}-(5-methyl[1,6]naphthyridin-2-yl)amine;
(5-Methyl[1,6]naphthyridin-2-yl)-{2-[4-(4-trifluoromethylphenoxy)piperidin-1-yl]ethyl}amine;
[2-(1-Benzylpiperidin-4-yl)ethyl]-(5-methyl[1,6]naphthyridin-2-yl)amine;
{1-[2-(5-Methyl[1,6]naphthyridin-2-ylamino)ethyl]piperidin-4-yl}diphenylmethanol;
[2-(4-Benzhydryloxypiperidin-1-yl)ethyl]-(5-methyl[1,6]naphthyridin-2-yl)amine,
{2-[4-(3,5-Dimethoxybenzyloxy)piperidin-1-yl]ethyl}-(5-methyl[1,6]naphthyridin-2-yl)amine
(5-Methyl[1,6]naphthyridin-2-yl)-{2-[4-(3-phenylpropyl)piperidin-1-yl]ethyl}amine;
1-[2-(5-Methyl[1,6]naphthyridin-2-ylamino)ethyl]piperidin-3-ol;
(5-Methyl[1,6]naphthyridin-2-yl)-{2-[4-(4-trifluoromethylbenzenesulfonyl)piperazin-1-yl]ethyl}amine;
4-{4-[2-(5-Methyl[1,6]naphthyridin-2-ylamino)ethyl]piperazine-1-sulfonyl}benzonitrile;
{2-[4-(4-Fluorobenzenesulfonyl)piperazin-1-yl]ethyl}-(5-methyl[1,6]naphthyridin-2-yl)amine;
{2-[4-(4-Methoxybenzenesulfonyl)piperazin-1-yl]ethyl}-(5-methyl[1,6]naphthyridin-2-yl)amine;
{2-[4-(6-Chloropyridine-3-sulfonyl)piperazin-1-yl]ethyl}-(5-methyl[1,6]naphthyridin-2-yl)amine;
[2-(4-Methanesulfonylpiperazin-1-yl)ethyl]-(5-methyl[1,6]naphthyridin-2-yl)amine;
(5-Methyl[1,6]naphthyridin-2-yl)-[2-(4-phenylmethanesulfonylpiperazin-1-yl)ethyl]amine;
{2-[4-(4-Bromobenzenesulfonyl)piperazin-1-yl]ethyl}-(5-methyl[1,6]naphthyridin-2-yl)amine;
{2-[4-(4-Chlorobenzenesulfonyl)piperazin-1-yl]ethyl}-(5-methyl[1,6]naphthyridin-2-yl)amine;
{2-[4-(4-Methanesulfonylbenzenesulfonyl)piperazin-1-yl]ethyl}-(5-methyl[1,6]naphthyridin-2-yl)amine;
{2-[4-(4-tert-Butylbenzenesulfonyl)piperazin-1-yl]ethyl}-(5-methyl[1,6]naphthyridin-2-yl)amine;
(5-Methyl[1,6]naphthyridin-2-yl)-{2-[4-(2,4,6-trichlorobenzenesulfonyl)piperazin-1-yl]ethyl}amine;
(5-Methyl[1,6]naphthyridin-2-yl)-{2-[4-(2-trifluoromethoxybenzenesulfonyl)piperazin-1-yl]ethyl}amine;
(5-Methyl[1,6]naphthyridin-2-yl)-{2-[4-(3-trifluoromethoxybenzenesulfonyl)piperazin-1-yl]ethyl}amine;
(5-Methyl[1,6]naphthyridin-2-yl)-{2-[4-(4-trifluoromethoxybenzenesulfonyl)piperazin-1-yl]ethyl}amine;
{2-[4-(4-Fluorobenzenesulfonyl)piperidin-1-yl]ethyl}-(5-methyl[1,6]naphthyridin-2-yl)amine;
N-{1-[2-(5-Methyl[1,6]naphthyridin-2-ylamino)ethyl]piperidin-4-yl}-C-phenylmethanesulfonamide;
N-{1-[2-(5-Methyl[1,6]naphthyridin-2-ylamino)ethyl]piperidin-4-yl}benzenesulfonamide;
N-{1-[2-(5-Methyl[1,6]naphthyridin-2-ylamino)ethyl]piperidin-4-yl}-4-trifluoromethylbenzenesulfonamide;
{2-[3-(4-Fluorobenzenesulfonyl)piperidin-1-yl]ethyl}-(5-methyl[1,6]naphthyridin-2-yl)amine;
1-[2-(5-Methyl[1,6]naphthyridin-2-ylamino)ethyl]piperidine-4-sulfonic acid benzhydrylamide;
{2-[3-(4-Fluorobenzenesulfonyl)pyrrolidin-1-yl]ethyl}-(5-methyl[1,6]naphthyridin-2-yl)amine;
{2-[4-(2,2-Diphenylethanesulfonyl)piperazin-1-yl]ethyl}-(5-methyl[1,6]naphthyridin-2-yl)amine;
{2-[4-(Diphenylmethanesulfonyl)piperazin-1-yl]ethyl}-(5-methyl[1,6]naphthyridin-2-yl)amine; and
1-{4-[2-(5-Methyl[1,6]naphthyridin-2-ylamino)ethyl]piperazin-1-yl}-3,3-diphenylpropan-1-one.

Example 8

Synthesis of (5-Methyl[1,6]naphthyridin-2-yl)-(2-piperazin-1-ylethyl)amine (8)

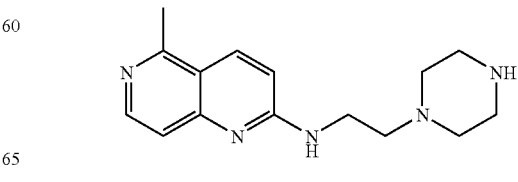

Compound 7 (211 mg, 0.57 mmol) was added to 10 mL of HCl in dioxane (4 N). It was stirred at room temperature overnight. The solvent was removed to afford compound 8 as the HCl salt (236.90 mg, 100%). $^1$H NMR (CD$_3$OD, 400 MHz) δ 8.30-8.45.9m, 2H), 7.82 (d, 7 Hz), 7.19 (d, 1H, J=7 Hz), 4.10-4.18 (m, 1H), 3.78-3.88 (m, 4H), 3.63-3.73 (m, 6H), 2.79 (s, 3H). LCMS (EI) m/z 272 (M+1).

Example 9

Synthesis of [2-(4-Benzylpiperazin-1-yl)ethyl]-(5-methyl[1,6]naphthyridin-2-yl)amine (9)

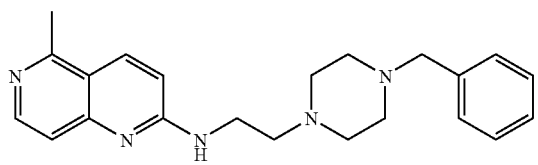

To a stirred solution of compound 8 (56.74 mg, 0.136 mmol) in DMF (10 mL) was added benzaldehyde (21.65 mg, 0.204), MP-triacetoxyborohydride (2.70 mmol/g, 302 mg, 0.816 mmol), and acetic acid (24.5 mg, 0.408 mmol). It was stirred at room temperature overnight. The resin was removed by filtration. The solvent was removed and chromatography on silica gel afforded compound 9 (46.0 mg, 93.6). $^1$H NMR (CD$_3$OD, 400 MHz) δ 8.19 (d, 1H, J=5.5 Hz), 8.09 (d, 1H, J=7.5 Hz), 7.20-7.35 (m, 6H), 6.81 (d, 1H, J=7.5 Hz), 3.62-3.71 (m, 2H), 3.55 (s, 2H), 2.75 (s, 3H), 2.45-2.70 (m, 10H). LCMS (EI) m/z 362 (M+1).

Example 10

Synthesis of (5-Methyl[1,6]naphthyridin-2-yl)-[2-(4-phenethylpiperazin-1-yl)ethyl]amine (10)

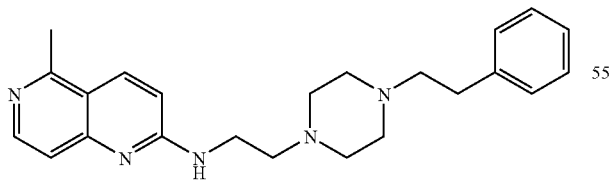

Compound 10 was prepared as described for compound 9, using phenylacetaldehyde in place of benzaldehyde. $^1$H NMR (CD$_3$OD, 400 MHz) δ 8.20 (d, 1H, J=5.5 Hz), 8.10 (d, 1H, J=7.5 Hz), 7.10-7.40 (m, 6H), 6.85 (d, 1H, J=7.5 Hz), 3.65-3.75 (m, 2H), 2.50-2.90 (m, 17H). LCMS (EI) m/z 376 (M+1).

Example 11

Synthesis of (5-Methyl[1,6]naphthyridin-2-yl)-{2-[4-(3-phenylpropyl)piperazin-1-yl]ethyl}amine (11)

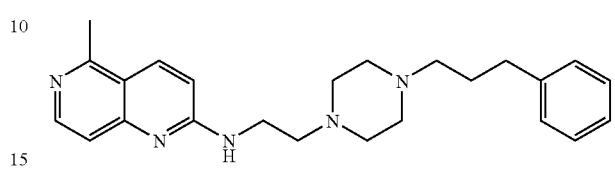

Compound 11 was prepared as described for compound 9, using 3-phenylpropionaldehyde in place of benzaldehyde. $^1$H NMR (CD$_3$OD, 400 MHz) δ 8.20 (d, 1H, J=5.5 Hz), 8.10 (d, 1H, J=7.5 Hz), 7.10-7.35 (m, 6H), 6.82 (d, 1H, J=7.5 Hz), 3.60-3.70 (m, 2H), 2.50-2.90 (m, 15H), 2.30-2.45 (m, 2H), 1.75-1.90 (m, 2H). LCMS (EI) m/z 390 (M+1).

Example 12

Synthesis of {2-[4-(4-Chlorophenyl)piperazin-1-yl]ethyl}-(5-methyl[1,6]naphthyridin-2-yl)amine (12)

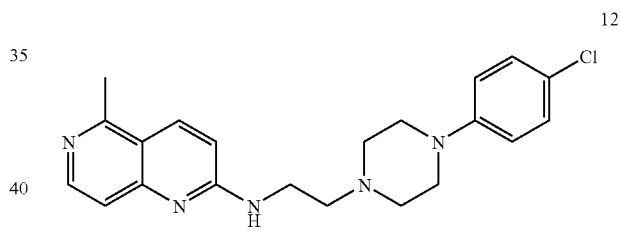

Compound 12 was prepared using the method described for compound 3, Method A. $^1$H NMR (CDCl$_3$, 400 MHz) δ 8.39 (d, 1H, J=5.5 Hz), 8.02 (d, 1H, J=8.0 Hz), 7.35 (d, 1H, J=5.5 Hz), 7.20-7.25 9m, 2H), 6.86 (d, 1H, J=7.0 Hz), 6.70 (d, 1H, J=7.0 Hz), 3.65-3.72 9m, 2H), 3.18-3.23 (m, 4H), 2.82 (s, 3H), 2.66-2.77 (m, 6H). LCMS (EI) m/z 382 (M+1).

Example 13

Synthesis of [2-(4-Benzenesulfonylpiperazin-1-yl)ethyl]-(5-methyl[1,6]naphthyridin-2-yl)amine (13)

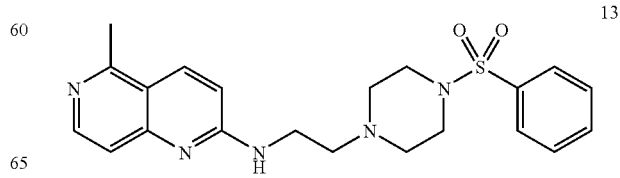

Compound 13 was prepared using the method described for compound 3, Method A. $^1$H NMR (CD$_3$OD, 400 MHz) δ 8.19 (d, 1H, J=5.5 Hz), 8.07 (d, 1H, J=8.0 Hz), 7.57-7.80 (m, 5H), 7.29 (d, 1H, J=6.0 Hz), 6.80 (d, 1H, J=7.5 Hz), 3.57-3.65 (m, 2H), 2.98-3.06 (m, 4H), 2.74 (s, 3H), 2.60-2.67 (m, 6H). LCMS (EI) m/z 412 (M+1).

Example 14

Synthesis of [2-(4-Benzylpiperidin-1-yl)ethyl]-(5,7-dimethyl[1,6]naphthyridin-2-yl)amine (14)

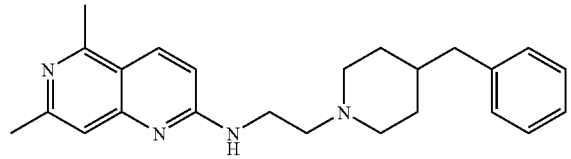

14

Compound 14 was prepared from compound 2 using the method described for compound 3, Method A, except that it was purified by prep-HPLC and was isolated as TFA salt. $^1$H NMR (CD$_3$OD, 400 MHz) δ 8.30 (d, 1H, J=8.0 Hz), 7.50 (s, 1H), 7.15-7.35 (m, 5H), 7.03 9d, 1H, J=8.0 Hz), 3.98-4.06 (m, 2H), 3.76-3.84 (m, 2H), 3.40-3.47 (m 2H), 2.90-3.08 (m, 5H), 2.70 (s, 3H), 2.58-2.65 (m, 2H), 1.82-2.00 (m, 3H), 1.45-1.60 (m, 2H). LCMS (EI) m/z 375 (M+1).

Example 15

[2-(4-Benzenesulfonylpiperazin-1-yl)ethyl]-(5,7-dimethyl[1,6]naphthyridin-2-yl)amine (15)

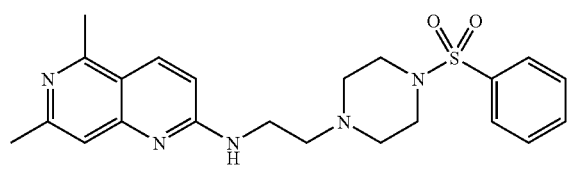

15

Compound 15 was prepared from compound 2 using the method described for compound 3, Method A, except that it was purified by prep-HPLC and was isolated as TFA salt. $^1$H NMR (CD$_3$OD, 400 MHz) δ 8.25 (d, 1H, J=7.5 Hz), 7.60-7.85 (m, 5H), 7.49 (s, 1H), 6.95-7.00 (d, 1H, J=7.5 Hz), 3.98-4.06 (m, 2H), 3.27-3.75 (m, 10H), 2.94 (s, 3H), 2.69 (s, 3H). LCMS (EI) m/z 426 (M+1).

The following example illustrates the method used to prepare 2-O-alkyoxynaphthyridines:

Example 16

Synthesis of 5-Methyl-2-(2-piperidin-1-ylethoxy)-[1,6]naphthyridine (16)

2-Piperidin-1-ylethanol (43 mg, 0.34 mmol) was treated with a 60% dispersion of NaH in mineral oil (17 mg, 0.42 mmol) in 2 mL of DMF. The mixture was stirred for 20 minutes and the 1,6-naphthyridine chloride was added, and the solution was stirred at 50° C. for 16 hours. The solution was cooled to room temperature and diluted with EtOAc and H$_2$O. The organic layer was separated and washed with saturated aqueous sodium bicarbonate solution (NaHCO$_3$) and brine, and dried over magnesium sulfate. The organics were filtered, concentrated, and purified by silica gel chromatography eluting with a gradient of dichloromethane/MeOH/NH$_4$OH to yield 33 mg (41%) of compound 16. LCMS (EI) m/z 274 (M+1).

The following compounds were made using procedures analogous to those described in Example 16:
5-Methyl-2-((R)-1-methylpyrrolidin-3-yloxy)-[1,6]naphthyridine;
Dimethyl-[2-(5-methyl[1,6]naphthyridin-2-yloxyethyl]amine;
5-Methyl-2-((S)-1-methylpyrrolidin-2-ylmethoxy)-[1,6]naphthyridine;
2-[3-(4-Benzylpiperidin-1-yl)propoxy]-5-methyl[1,6]naphthyridine;
5-Methyl-2-(2-pyrrolidin-1-ylethoxy)-[1,6]naphthyridine;
Benzylmethyl-[2-(5-methyl[1,6]naphthyridin-2-yloxy)ethyl]amine;
[2-(4-Benzylpiperidin-1-yl)ethyl]-(5,7-dimethylquinolin-2-yl)amine;
Dimethyl-[2-(5-methyl[1,6]naphthyridin-2-yloxy)propyl]amine;
[2,2-Dimethyl-3-(5-methyl[1,6]naphthyridin-2-yloxy)propyl]dimethylamine;
2-(1-Benzylpiperidin-4-yloxy)-5-methyl[1,6]naphthyridine;
2-(1-Benzylpiperidin-3-yloxy)-5-methyl[1,6]naphthyridine;
5-Methyl-2-(2-morpholin-4-ylethoxy)-[1,6]naphthyridine;
2-(1-Isopropylpyrrolidin-3-yloxy)-5-methyl[1,6]naphthyridine;
2-(1-Ethylpyrrolidin-3-yloxy)-5-methyl[1,6]naphthyridine;
2-((S)-1-Benzylpyrrolidin-2-ylmethoxy)-5-methyl[1,6]naphthyridine;
1-[2-(5-Methyl[1,6]naphthyridin-2-yloxy)ethyl]imidazolidin-2-one;

5-Methyl-2-[2-(4-methylpiperazin-1-yl)ethoxy]-[1,6]naphthyridine;
5-Methyl-2-[3-(4-methylpiperazin-1-yl)propoxy]-[1,6]naphthyridine; and
2-[2-(4-Benzylpiperidin-1-yl)ethoxy]-5-methyl[1,6]naphthyridine.

Example 17

Synthesis of 2-(4-Benzylpiperidin-1-yl)-N-(5-methyl[1,6]naphthyridin-2-yl)acetamide (17)

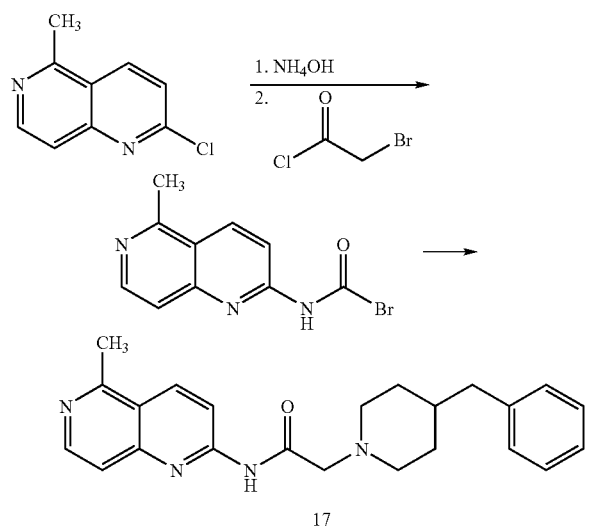

The following compounds were made using procedures analogous to those described in Example 17:
5-Methyl[1,6]naphthyridin-2-yl)amine;
N-(5-Methyl[1,6]naphthyridin-2-yl)-2-[4-(pyrimidin-2-yloxy)piperidin-1-yl]acetamide; and
N-(5-Methyl[1,6]naphthyridin-2-yl)-2-[4-(pyrimidin-2-ylamino)piperidin-1-yl]acetamide.

Example 18

Synthesis of 1-[2-(4-Benzylpiperidin-1-yl)ethyl]-3-(5-methyl[1,6]naphthyridin-2-yl)urea (18)

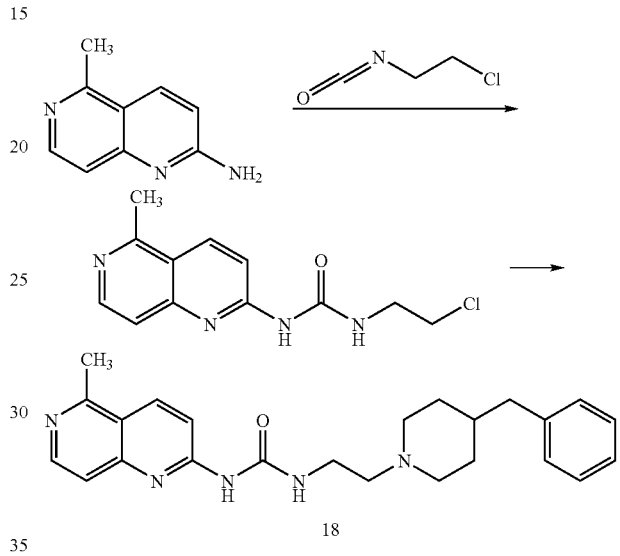

A mixture of 5-methylnaphthyridine chloride (998 mg, 5.59 mmol) and 20 mL of ammonium hydroxide in a microwave reaction tube was heated under microwave irradiation at 150° C. for 60 minutes. The solution was concentrated and the resultant red solid (817 mg, 92%) was taken on without further purification.

To a solution of 2-aminonaphthyridine (130 mg, 0.82 mmol) in 2 mL of dichloromethane at 0° C. was added pyridine (0.093 mL, 1.18 mmol) and bromoacetyl chloride (130 mg, 0.82 mmol) was added dropwise in a solution in 1 mL of dichloromethane. The reaction was allowed to warm to room temperature over 30 minutes then stirred an additional 2 hours at ambient temperature. The reaction mixture was then diluted with EtOAc (100 mL), washed with three 50 mL portions of saturated aqueous sodium bicarbonate solution, and dried over magnesium sulfate. The crude product was filtered and concentrated to obtain 228 mg (99%) of a product which was taken on without further purification.

The bromoacetamide intermediate (50 mg, 0.2 mmol) was added to a stirred solution of 4-benzylpiperidine (0.03 mg, 0.18 mmol) and sodium carbonate (0.028 mg, 0.268 mmol) in acetone (2 mL) at 0° C. It was then stirred at room temperature for 16 hours. The mixture was then concentrated and the resultant solid was triturated with water (5 mL), then diluted with 20 mL of ether and washed with two 10 mL portions of water, and dried over sodium sulfate. The crude product was filtered, concentrated, and purified by silica gel chromatography eluting with a gradient of dichloromethane/MeOH/NH$_4$OH to obtain 27 mg (40%) of compound 17. LCMS (EI) m/z 375 (M+1).

To a stirred solution of the 2-aminonaphthyridine intermediate (300 mg, 1.9 mmol) in 10 mL of THF was added 2-chloroethylisocyanate (0.298 mg, 2.83 mmol). The reaction mixture was stirred at room temperature for 48 hours. It was concentrated, then diluted with dichloromethane (10 mL), the precipitates formed were isolated by filtration. The product was purified by silica gel chromatography eluting with a gradient of dichloromethane/MeOH to obtain 230 mg (47%) of an off-white solid.

To a stirred solution of the ethylurea-naphthyridine intermediate (44 mg, 0.17 mmol) in 2 mL of DMF was added 4-benzylpiperidine (44 mg, 0.25 mmol) and sodium carbonate (0.141 g, 1.33 mmol). The reaction mixture was heated at 50° C. for 48 hours. The mixture was diluted with water (10 mL), extracted with two 10 mL portions of dichloromethane, and washed with brine (10 mL). The organic layer was dried over sodium sulfate, and purified by silica gel chromatography eluting with a gradient of dichloromethane/MeOH/NH$_4$OH to yield 18 mg (27%) of desired. LCMS (EI) m/z 404 (M+1).

Assessment of Biological Activity

Test compounds were evaluated for their ability to inhibit U-II-stimulated Ca$^{2+}$ mobilization in a CHO cell line expressing the human U-II receptor.

Inhibition of Ca$^{2+}$ Mobilization in a Human U-II Receptor-Expressing Clone (FLIPR Assay, IC$_{50}$ Determination)

Materials: Ham's F12 (Cat. No. 1042120), Biomedicals, LLC (USA); FBS (Cat. No. 100-106), Puromycin (Cat. No. P7255) and Probenecid (Cat. No. P8761), Sigma (USA); G418 (Cat. No. 16512-52) and Trypsin/EDTA (Cat. No. 35554-64) Nacalai Tesque (Japan), DMSO (Cat. 048-21985), Wako Pure Chemical Industries Ltd. (Japan). Fluo-4 A$^M$ (Cat. No. F3111), Dojindo Laboratories (Japan); GIBCO™ 10× Hanks' balanced salt solution (HBSS) (Cat. No. 14065-056), Invitrogen (USA); Human urotensin II (Cat. No. 4365-v), Peptide Institute Inc. (Japan). 96-well black clear bottom plate (Cat. No. 3603), Corning Corster (USA). All other materials were of highest grade commercially available.

The recombinant CHO cell line (UroII-A5) expressing the human urotensin II receptor was purchased from Euroscreen s.a. (Belgium).

Method:

Culture medium: Ham's F12 including 400 g/mL G418, 5 g/mL puromycin and 10% FBS

Assay buffer: HBSS including 0.35 g/l NaHCO$_3$, 20 mM HEPES, and 2.5 mM probenecid* (*Add 1/100 (v/v) of 250 mM probenecid (1.42 g/10 mL of 0.1N NaOH) the day of the assay)

Fluo-4 loading buffer: 4 µM Fluo-4 A$^M$ in the assay buffer including 0.1% BSA

Ligand solution for stimulation: Human U-II is dissolved in water to prepare a stock solution at 100 µM, and stored at −20° C. The stock solution is diluted with the assay buffer including 0.1% BSA at 30 nM.

Test compound solution for stock and assay: Test compound is dissolved in 100% DMSO to prepare a stock solution at 3 mM, and stored at −20° C. The stock solution is sequentially diluted with the assay buffer to appropriate concentrations (2-fold higher concentrations of the final concentrations).

Ca$^{2+}$ measurements with FLIPR

The day before the experiment, UroII-A5 cells are detached from the culture dish with PBS including 0.25% trypsin and 1 mM EDTA, and resuspended at 2.5×10$^5$ cells/mL in Ham's F12 supplemented with 10% FBS. The cells are seeded into a 96 well plate at a density of 2.5×10$^4$ cells/well and incubated overnight.

The culture medium is drained and the wells are washed with the assay buffer (200 µL, 3 times) using a microplate washer (PW384, TECAN, Austria). The wells are filled with 50 µL of the assay buffer and loaded with 50 µL of the Fluo-4 AM solution at the final concentration of 2 µM. The plate is then incubated for 1 hour at 37° C. The wells are washed with the assay buffer (200 µL, 7 times) to remove excess unloaded dye, and filled with 100 µl of the assay buffer or 50 µL of the compound solution and 50 µl of the assay buffer. The plate is further incubated for 20 minutes at room temperature. After setting the plate in the FLIPR96 (Molecular Devices, USA), 50 µL of the human U-II solution is added at final concentration of 1.0 nM. The fluorescence output is measured at 500 to 560 nm.

Data analysis: IC$_{50}$ values of tested compounds are calculated by nonlinear regression using the program Prism (GraphPad Software, USA). The mean of the IC$_{50}$ values is obtained from two independent experiments in triplicate or quadruplicate.

Preferred compounds had an IC$_{50}$<10 µM in this assay. More preferred compounds had an IC$_{50}$ less than 1 µM in this assay.

Test compounds were evaluated for their ability to inhibit binding of labeled U-II to its receptor.

Inhibition of $^{125}$I-U-II Binding to Human U-II Receptors

Materials: 96-well Dynax microfluor 2 white U-bottom plates were purchased from VWR (62402-970). The radioligand $^{125}$I-U-II (Cat. No. IM339; spec. act. approx. 2000 Ci/mmol) was purchased from Amersham. The membranes from Chem-2 cells stably expressing the human recombinant GPR14/U-II receptor were purchased from Chemicon.

The wheat germ agglutinin (WGA) coupled PVT SPA beads (Cat. No. NIF1633) were from Amersham Biosciences. All other materials were of highest grade commercially available.

Method: In the 96-well plates, 10 µL test compound in 7% DMSO-assay buffer (final concentration of compound 10 µM; DMSO 1%) are mixed with 20 µL of a mixture of WGA beads (15 mg/mL) and U-II membranes (125 µg/mL), and 20 µL $^{125}$I-U-II ligand (~1,500,000 dpm/mL). All solutions/suspensions are prepared in assay buffer. The plates are then sealed and incubated in the dark at room temperature for at least 4 hours. After the incubation period the membrane bound radioactivity of the scintillation proximity assay is determined by reading the scintillation intensity of the plate/wells in the Topcount instrument for 60 seconds/well.

Assay buffer: 25 mM Tris pH 7.5, 5 mM MgCl$_2$, 0.3% BSA

Each assay microtiter plate contains wells with vehicle controls instead of compound (1% DMSO in assay buffer) as reference for total binding (100% CTL; high values) and wells without membrane as controls for non-specific binding (0% CTL; low values). The analysis of the data is performed by the calculation of the percentage of specifically bound radioactivity in the presence of the test compound compared to the specifically bound radioactivity of the vehicle control after subtraction of the non-specific binding:

$$\% \text{ inhibition} = \frac{100 - ((IOD(\text{sample}) - IOD(\text{non-specific}))}{(IOD(\text{total binding}) - IOD(\text{non-specific}) * 100))}$$

An inhibitor of the receptor binding of the radioligand $^{125}$I-U-II will give values between 0% inhibition and 100% inhibition (complete inhibition) after taking the variability of the assay into account. Values of more than 100% CTL are normally related to compound-specific physico-chemical properties (e.g., solubility, fluorescence) or indirect biochemical effects such as allosteric regulation.

Preferred compounds had an IC$_{50}$<10 µM in this assay.

Methods of Therapeutic Use

As pointed out above, the compounds of the invention are useful in inhibiting U-II. In doing so, these compounds have therapeutic use in treating disease-states and conditions mediated by the U-II or that would benefit from modulation of the U-II activity.

As the compounds of the invention modulate U-II activity, they have very useful activity and they can be used in patients as drugs, particularly in the form of pharmaceutical compositions as set forth below, for the treatment of disease-states and conditions.

The inhibitory compounds according to the invention can be used in patients as drugs for the treatment of cardiovascular or related disease-states or indications. Examples of such diseases include, for example, hypertension, stroke, heart failure, renal failure, myocardial infarction, coronary artery disease, peripheral artery disease and atherosclerosis.

In another aspect, the present invention is directed to a method of treating diabetes or cirrhosis comprising administering to an individual a compound described above.

Methods of Diagnostic Use

The compounds of the invention may also be used in diagnostic applications and for commercial and other purposes as standards in competitive binding assays. In such uses, the compounds of the invention may be used in the form of the compounds themselves or they may be modified by attaching a radioisotope, luminescence, fluorescent label or the like in order to obtain a radioisotope, luminescence, or fluorescent probe, as would be known by one of skill in the art and as outlined in *Handbook of Fluorescent Probes and Research Chemicals,* 6th Edition, R. P. Haugland (ed.), Eugene: Molecular Probes, 1996; *Fluorescence and Luminescence Probes for Biological Activity*, W. T. Mason (ed.), San Diego: Academic Press, 1993; *Receptor-Ligand Interaction, A Practical Approach*, E. C. Hulme (ed.), Oxford: IRL Press, 1992, each of which is hereby incorporated by reference in their entireties.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, or in conjunction with other pharmacologically active substances including diuretics, beta blockers, angiotensin converting enzyme inhibitors, angiotensin blockers and calcium channel blockers. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy,* 20th Edition, A. Gennaro (ed.), Lippincott Williams & Wilkins, 2000; *Handbook of Pharmaceutical Additives,* Michael & Irene Ash (eds.), Gower, 1995; *Handbook of Pharmaceutical Excipients,* A. H. Kibbe (ed.), American Pharmaceutical Ass'n, 2000; H. C. Ansel and N. G. Popovish, *Pharmaceutical Dosage Forms and Drug Delivery Systems,* 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

Pharmaceutical compositions suitable for buccal (sub-lingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration comprise sterile aqueous preparations of a compound of the present invention. These preparations are preferably administered intravenously, although administration can also be effected by means of subcutaneous, intramuscular, or intradermal injection. Injectable pharmaceutical formulations are commonly based upon injectable sterile saline, phosphate-buffered saline, oleaginous suspensions, or other injectable carriers known in the art and are generally rendered sterile and isotonic with the blood. The injectable pharmaceutical formulations may therefore be provided as a sterile injectable solution or suspension in a nontoxic parenterally acceptable diluent or solvent, including 1,3-butanediol, water, Ringer's solution, isotonic sodium chloride solution, fixed oils such as synthetic mono- or diglycerides, fatty acids such as oleic acid, and the like. Such injectable pharmaceutical formulations are formulated according to the known art using suitable dispersing or setting agents and suspending agents. Injectable compositions will generally contain from 0.1 to 5% w/w of a compound of the invention.

Solid dosage forms for oral administration of the compounds include capsules, tablets, pills, powders, and granules. For such oral administration, a pharmaceutically acceptable composition containing a compound(s) of the invention is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such solid pharmaceutical formulations may include formulations, as are well-known in the art, to provide prolonged or sustained delivery of the drug to the gastrointestinal tract by any number of mechanisms, which include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form.

Liquid dosage forms for oral administration of the compounds include emulsions, microemulsions, solutions, suspensions, syrups, and elixirs, optionally containing pharmaceutical adjuvants in a carrier, such as, for example, water, saline, aqueous dextrose, glycerol, ethanol and the like. These compositions can also contain additional adjuvants such as wetting, emulsifying, suspending, sweetening, flavoring, and perfuming agents.

Topical dosage forms of the compounds include ointments, pastes, creams, lotions, gels, powders, solutions, sprays, inhalants, eye ointments, eye or ear drops, impregnated dressings and aerosols, and may contain appropriate conventional additives such as preservatives, solvents to assist drug penetration and emollients in ointments and creams. Topical application may be once or more than once per day depending upon the usual medical considerations. Furthermore, preferred compounds for the present invention can be administered in intranasal form via topical use of suitable intranasal vehicles. The formulations may also contain compatible conventional carriers, such as cream or ointment bases and ethanol or oleyl alcohol for lotions. Such carriers may be present as from about 1% up to about 98% of the formulation, more usually they will form up to about 80% of the formulation.

Transdermal administration is also possible. Pharmaceutical compositions suitable for transdermal administration can be presented as discrete patches adapted to remain in intimate contact with the epidermis of the recipient for a prolonged period of time. To be administered in the form of a transdermal delivery system, the dosage administration will, of course, be continuous rather than intermittent throughout the dosage regimen. Such patches suitably contain a compound of the invention in an optionally buffered, aqueous solution, dissolved and/or dispersed in an adhesive, or dispersed in a polymer. A suitable concentration of the active compound is about 1% to 35%, preferably about 3% to 15%.

For administration by inhalation, the compounds of the invention are conveniently delivered in the form of an aerosol spray from a pump spray device not requiring a propellant gas or from a pressurized pack or a nebulizer with the use of a suitable propellant, e.g., dichlorodifluoromethane, trichlorofluoromethane, dichlorotetrafluoroethane, tetrafluoroethane, heptafluoropropane, carbon dioxide, or other suitable gas. In any case, the aerosol spray dosage unit may be determined by providing a valve to deliver a metered amount so that the resulting metered dose inhaler (MDI) is used to administer the compounds of the invention in a reproducible and controlled way. Such inhaler, nebulizer, or atomizer devices are known in the prior art, for example, in PCT International Publication Nos. WO 97/12687 (particularly FIG. 6 thereof, which is the basis for the commercial RESPIMAT® nebulizer); WO 94/07607; WO 97/12683; and WO 97/20590, to which reference is hereby made and each of which is incorporated herein by reference in their entireties.

Rectal administration can be effected utilizing unit dose suppositories in which the compound is admixed with low-melting water-soluble or insoluble solids such as fats, cocoa butter, glycerinated gelatin, hydrogenated vegetable oils, mixtures of polyethylene glycols of various molecular weights, or fatty acid esters of polyethylene glycols, or the like. The active compound is usually a minor component, often from about 0.05 to 10% by weight, with the remainder being the base component.

In all of the above pharmaceutical compositions, the compounds of the invention are formulated with an acceptable carrier or excipient. The carriers or excipients used must, of course, be acceptable in the sense of being compatible with the other ingredients of the composition and must not be deleterious to the patient. The carrier or excipient can be a solid or a liquid, or both, and is preferably formulated with the compound of the invention as a unit-dose composition, for example, a tablet, which can contain from 0.05% to 95% by weight of the active compound. Such carriers or excipients include inert fillers or diluents, binders, lubricants, disintegrating agents, solution retardants, resorption accelerators, absorption agents, and coloring agents. Suitable binders include starch, gelatin, natural sugars such as glucose or β-lactose, corn sweeteners, natural and synthetic gums such as acacia, tragacanth or sodium alginate, carboxymethylcellulose, polyethylene glycol, waxes, and the like. Lubricants include sodium oleate, sodium stearate, magnesium stearate, sodium benzoate, sodium acetate, sodium chloride, and the like. Disintegrators include starch, methyl cellulose, agar, bentonite, xanthan gum, and the like.

Generally, a therapeutically effective daily dose is from about 0.001 mg to about 15 mg/kg of body weight per day of a compound of the invention; preferably, from about 0.1 mg to about 10 mg/kg of body weight per day; and most preferably, from about 0.1 mg to about 1.5 mg/kg of body weight per day. For example, for administration to a 70 kg person, the dosage range would be from about 0.07 mg to about 1050 mg per day of a compound of the invention, preferably from about 7.0 mg to about 700 mg per day, and most preferably from about 7.0 mg to about 105 mg per day. Some degree of routine dose optimization may be required to determine an optimal dosing level and pattern.

Pharmaceutically acceptable carriers and excipients encompass all the foregoing additives and the like.

Examples of Pharmaceutical Formulations

| A. TABLETS | |
| --- | --- |
| Component | Amount per tablet (mg) |
| active substance | 100 |
| lactose | 140 |
| corn starch | 240 |
| polyvinylpyrrolidone | 15 |
| magnesium stearate | 5 |
| TOTAL | 500 |

The finely ground active substance, lactose, and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B. TABLETS | |
| --- | --- |
| Component | Amount per tablet (mg) |
| active substance | 80 |
| lactose | 55 |
| corn starch | 190 |
| polyvinylpyrrolidone | 15 |
| magnesium stearate | 2 |
| microcrystalline cellulose | 35 |
| sodium-carboxymethyl starch | 23 |
| TOTAL | 400 |

The finely ground active substance, some of the corn starch, lactose, microcrystalline cellulose, and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| C. COATED TABLETS | |
| --- | --- |
| Component | Amount per tablet (mg) |
| active substance | 5 |
| lactose | 30 |
| corn starch | 41.5 |
| polyvinylpyrrolidone | 3 |
| magnesium stearate | 0.5 |
| TOTAL | 90 |

The active substance, corn starch, lactose, and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

| D. CAPSULES | |
|---|---|
| Component | Amount per capsule (mg) |
| active substance | 50 |
| corn starch | 268.5 |
| magnesium stearate | 1.5 |
| TOTAL | 320 |

The substance and corn starch are mixed and moistened with water. The moist mass is screened and dried. The dry granules are screened and mixed with magnesium stearate. The finished mixture is packed into size 1 hard gelatine capsules.

| E. AMPOULE SOLUTION | |
|---|---|
| Component | Amount per ampoule |
| active substance | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilized and sealed by fusion. The ampoules contain 5 mg, 25 mg, and 50 mg of active substance.

| F. SUPPOSITORIES | |
|---|---|
| Component | Amount per suppository (mg) |
| active substance | 50 |
| solid fat | 1650 |
| TOTAL | 1700 |

The hard fat is melted. At 40° C., the ground active substance is homogeneously dispersed therein. The mixture is cooled to 38° C. and poured into slightly chilled suppository molds.

| G. METERING AEROSOL | |
|---|---|
| Component | Amount |
| active substance | 0.005 |
| sorbitan trioleate | 0.1 |
| monofluorotrichloromethane and difluorodichloromethane (2:3) | to 100 |

The suspension is transferred into a conventional aerosol container with a metering valve. Preferably, 50 µL of suspension are delivered per spray. The active substance may also be metered in higher doses if desired (e.g., 0.02% by weight).

| H. POWDER FOR INHALATION | |
|---|---|
| Component | Amount |
| active substance | 1.0 mg |
| lactose monohydrate | to 25 mg |

| I. POWDER FOR INHALATION | |
|---|---|
| Component | Amount |
| active substance | 2.0 mg |
| lactose monohydrate | to 25 mg |

| J. POWDER FOR INHALATION | |
|---|---|
| Component | Amount |
| active substance | 1.0 mg |
| lactose monohydrate | to 5 mg |

| K. POWDER FOR INHALATION | |
|---|---|
| Component | Amount |
| active substance | 2.0 mg |
| lactose monohydrate | to 5 mg |

In Examples H, I, J, and K, the powder for inhalation is produced in the usual way by mixing the individual ingredients together.

We claim:
1. A compound of the formula (I)

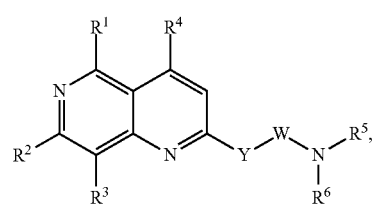

wherein:
$R^1$ is $C_{1-3}$-alkyl;
$R^2$, $R^3$, and $R^4$ are each H;
Y is —NH—;
W is —$(CH_2)_n$—, wherein n is 2 or 3;
$R^5$ and $R^6$, together with the N they are bonded to, are a pyrrolidinyl, piperidinyl, piperazinyl, morpholinyl, or azepanyl group, each optionally independently substituted with one to three groups selected from phenyl, phenyl-$C_{1-3}$-alkyl, phenyl-$SO_2$—, phenyl-$C_{0-1}$-alkyloxy, diphenylhydroxymethyl, diphenylmethoxy, $C_{1-3}$-alkyl, —$CO_2C_{1-6}$-alkyl, and OH, wherein each phenyl is optionally independently substituted with one to three $R_7$; and $R_7$ is $C_{1-6}$-alkyl, $C_{1-6}$-alkoxy, Cl, F, —OH, —$OCF_3$, or $CF_3$, or a tautomer, or salt thereof.

2. A compound selected from:

5-Methyl-2-((R)-1-methylpyrrolidin-3-yloxy)-[1,6]naphthyridine;
Dimethyl-[2-(5-methyl[1,6]naphthyridin-2-yloxy)ethyl]amine;
[2-(4-Benzylpiperidin-1-yl)ethyl]-(5-methyl[1,6]naphthyridin-2-yl)amine;
(5-Methyl[1,6]naphthyridin-2-yl)-(2-piperidin-1-ylethyl)amine;
1-[2-(5-Methyl[1,6]naphthyridin-2-ylamine)ethyl]piperidin-4-ol;
4-Benzyl-1-[2-(5-methyl[1,6]naphthyridin-2-ylamino)ethyl]piperidin-4-ol;
4-[2-(5-Methyl[1,6]naphthyridin-2-ylamino)ethyl]piperazine-1-carboxylic acid tert-butyl ester;
(5-Methyl[1,6]naphthyridin-2-yl)-(2-piperazin-1-ylethyl)amine;
[2-(4-Benzylpiperazin-1-yl)ethyl]-(5-methyl[1,6]naphthyridin-2-yl)amine;
{2-[4-(4-Chlorophenyl)piperazin-1-yl]ethyl}-(5-methyl-1-[1,6]naphthyridin-2-yl)amine;
[2-(4-Benzenesulfonylpiperazin-1-yl)ethyl]-(5-methyl[1,6]naphthyridin-2-yl)amine;
(5-Methyl[1,6]naphthyridin-2-yl)-{2-[4-(3-phenylpropyl)piperazin-1-yl]ethyl}amine;
(5-Methyl[1,6]naphthyridin-2-yl)-[2-(4-phenethylpiperazin-1-yl)ethyl]amine;
[2-(4-Benzylpiperidin-1-yl)ethyl]-(5,7-dimethyl[1,6]naphthyridin-2-yl)amine;
[2-(4-Benzenesulfonylpiperazin-1-yl)ethyl]-(5,7-dimethyl[1,6]naphthyridin-2-yl)amine;
5-Methyl-2-((S)-1-methylpyrrolidin-2-ylmethoxy)-[1,6]naphthyridine;
[2-(4-Benzylpiperidin-1-yl)ethyl]-(5-phenyl[1,6]naphthyridin-2-yl)amine;
N,N-Dimethyl-N'-(5-methyl[1,6]naphthyridin-2-yl)ethane-1,2-diamine;
[2-(4-Benzylpiperidin-1-yl)ethyl]-(5-isopropyl[1,6]naphthyridin-2-yl)amine;
[2-(4-Benzylpiperidin-1-yl)ethyl]-(5-ethyl[1,6]naphthyridin-2-yl)amine;
[2-(4-Benzylpiperidin-1-yl)ethyl]-[1,6]naphthyridin-2-ylamine;
2-[3-(4-Benzylpiperidin-1-yl)propoxy]-5-methyl[1,6]naphthyridine;
[2-(4-Benzylpiperidin-1-yl)ethyl]-(7-methyl[1,6]naphthyridin-2-yl)amine;
(5-Methyl[1,6]naphthyridin-2-yl)-[2-(4-phenethylpiperidin-1-yl)ethyl]amine;
5-Methyl-2-(2-piperidin-1-ylethoxy)-[1,6]naphthyridine;
5-Methyl-2-(2-pyrrolidin-1-ylethoxy)-[1,6]naphthyridine;
Benzylmethyl-[2-(5-methyl[1,6]naphthyridin-2-yloxy)ethyl]amine;
Dimethyl-[2-(5-methyl[1,6]naphthyridin-2-yloxy)propyl]amine;
[2,2-Dimethyl-3-(5-methyl[1,6]naphthyridin-2-yloxy)propyl]dimethylamine;
2-(1-Benzylpiperidin-4-yloxy)-5-methyl[1,6]naphthyridine;
2-(1-Benzylpiperidin-3-yloxy)-5-methyl[1,6]naphthyridine;
5-Methyl-2-(2-morpholin-4-ylethoxy)-[1,6]naphthyridine;
2-(1-Isopropylpyrrolidin-3-yloxy)-5-methyl[1,6]naphthyridine;
2-(1-Ethylpyrrolidin-3-yloxy)-5-methyl[1,6]naphthyridine;
2-((S)-1-Benzylpyrrolidin-2-ylmethoxy)-5-methyl[1,6]naphthyridine;
1-[2-(5-Methyl[1,6]naphthyridin-2-yloxy)ethyl]imidazolidin-2-one;
5-Methyl-2-[2-(4-methylpiperazin-1-yl)ethoxy]-[1,6]naphthyridine;
5-Methyl-2-[3-(4-methylpiperazin-1-yl)propoxy]-[1,6]naphthyridine;
2-[2-(4-Benzylpiperidin-1-yl)ethoxy]-5-methyl[1,6]naphthyridine;
[2-(4-Benzylpiperidin-1-yl)ethyl]-(5-methoxy-7-methyl[1,6]naphthyridin-2-yl)amine;
[2-(4-Benzyloxypiperidin-1-yl)ethyl]-(5-methyl[1,6]naphthyridin-2-yl)amine;
(5-Methyl[1,6]naphthyridin-2-yl)-(3-morpholin-4-ylpropyl)amine;
((S)-1-Benzylpyrrolidin-3-yl)-(5-methyl[1,6]naphthyridin-2-yl)amine;
2,2, N,N-Tetramethyl-N'-(5-methyl[1,6]naphthyridin-2-yl)propane-1,3-diamine;
N,N-Dimethyl-N'-(5-methyl[1,6]naphthyridin-2-yl)propane-1,3-diamine;
(1-Ethylpyrrolidin-2-ylmethyl)-(5-methyl[1,6]naphthyridin-2-yl)amine;
(5-Methyl[1,6]naphthyridin-2-yl)-(2-pyrrolidin-1-ylethyl)amine;
1-[3-(5-Methyl[1,6]naphthyridin-2-ylamino)propyl]pyrrolidin-2-one;
N,N-Diisopropyl-N'-(5-methyl[1,6]naphthyridin-2-yl)ethane-1,2-diamine;
1-[2-(5-Methyl[1,6]naphthyridin-2-ylamino)ethyl]pyrrolidin-2-one;
(2-Azepan-1-ylethyl)-(5-methyl[1,6]naphthyridin-2-yl)amine;
(1-Benzylpyrrolidin-3-yl)-(5-methyl-[1,6]naphthyridin-2-yl)amine;
(5-Methyl[1,6]naphthyridin-2-yl)-[3-(4-methylpiperazin-1-yl)propyl]amine;
(5-Methyl[1,6]naphthyridin-2-yl)-[2-(2-methylpyrrolidin-1-yl)ethyl]amine;
(3-Azepan-1-ylpropyl)-(5-methyl[1,6]naphthyridin-2-yl)amine;
[3-(4-Benzylpiperidin-1-yl)propyl]-(5-methyl[1,6]naphthyridin-2-yl)amine;
(5-Methyl[1,6]naphthyridin-2-yl)-[3-(2-methylpiperidin-1-yl)propyl]amine;
(5-Methyl[1,6]naphthyridin-2-yl)-(3-piperidin-1-ylpropyl)amine;
2-[(4-Benzylpiperidin-1-yl)ethyl]methyl-(5-methyl[1,6]naphthyridin-2-yl)amine;
[3-(2,6-Dimethylpiperidin-1-yl)propyl]-(5-methyl[1,6]naphthyridin-2-yl)amine;
2-(4-Benzylpiperidin-1-yl)-N-(5-methyl[1,6]naphthyridin-2-yl)acetamide;
{2-[4-(4-Fluorophenoxy)piperidin-1-yl]ethyl}-(5-methyl[1,6]naphthyridin-2-yl)amine;
N-(5-Methyl[1,6]naphthyridin-2-yl)-{2-[4-(4-trifluoromethylphenoxy)piperidin-1-yl]ethyl}amine;

N-(5-Methyl[1,6]naphthyridin-2-yl)-2-[4-(pyrimidin-2-yloxy)piperidin-1-yl]acetamide;
N-(5-Methyl[1,6]naphthyridin-2-yl)-2-[4-(pyrimidin-2-ylamino)piperidin-1-yl]acetamide;
[2-(1-Benzylpiperidin-4-yl)ethyl]-(5-methyl[1,6]naphthyridin-2-yl)amine;
{1-[2-(5-Methyl[1,6]naphthyridin-2-ylamino)ethyl]piperidin-4-yl}diphenylmethanol;
1-[2-(4-Benzylpiperidin-1-yl)ethyl]-3-(5-methyl[1,6]naphthyridin-2-yl)urea;
[2-(4-Benzhydryloxypiperidin-1-yl)ethyl]-(5-methyl[1,6]naphthyridin-2-yl)amine;
{2-[4-(3,5-Dimethoxybenzyloxy)piperidin-1-yl]ethyl}-(5-methyl[1,6]naphthyridin-2-yl)amine;
(5-Methyl[1,6]naphthyridin-2-yl)-{2-[4-(5-methyl[1,6]naphthyridin-2-yl)piperazin-1-yl]ethyl}amine;
(5-Methyl[1,6]naphthyridin-2-yl)-{2-[4-(3-phenylpropyl)piperidin-1-yl]ethyl}amine;
1-[2-(5-Methyl[1,6]naphthyridin-2-ylamino)ethyl]piperidin-3-ol;
(5-Methyl[1,6]naphthyridin-2-yl)-{2-[4-(4-trifluoromethylbenzenesulfonyl)piperazin-1-yl]ethyl}amine;
4-{4-[2-(5-Methyl[1,6]naphthyridin-2-ylamino)ethyl]piperazine-1-sulfonyl}benzonitrile;
{2-[4-(4-Fluorobenzenesulfonyl)piperazin-1-yl]ethyl}-(5-methyl[1,6]naphthyridin-2-yl)amine;
{2-[4-(4-Methoxybenzenesulfonyl)piperazin-1-yl]ethyl}-(5-methyl[1,6]naphthyridin-2-yl)amine;
{2-[4-(6-Chloropyridine-3-sulfonyl)piperazin-1-yl]ethyl}-(5-methyl[1,6]naphthyridin-2-yl)amine;
[2-(4-Methanesulfonylpiperazin-1-yl)ethyl]-(5-methyl[1,6]naphthyridin-2-yl)amine;
(5-Methyl[1,6]naphthyridin-2-yl)-[2-(4-phenylmethanesulfonylpiperazin-1-yl)ethyl]amine;
{2-[4-(4-Bromobenzenesulfonyl)piperazin-1-yl]ethyl}-(5-methyl[1,6]naphthyridin-2-yl)amine;
{2-[4-(4-Chlorobenzenesulfonyl)piperazin-1-yl]ethyl}-(5-methyl[1,6]naphthyridin-2-yl)amine;
{2-[4-(4-Methanesulfonylbenzenesulfonyl)piperazin-1-yl]ethyl}-(5-methyl[1,6]naphthyridin-2-yl)amine;
{2-[4-(4-tert-Butylbenzenesulfonyl)piperazin-1-yl]ethyl}-(5-methyl[1,6]naphthyridin-2-yl)amine;
(5-Methyl[1,6]naphthyridin-2-yl)-{2-[4-(2,4,6-trichlorobenzenesulfonyl)piperazin-1-yl]ethyl}amine;
(5-Methyl[1,6]naphthyridin-2-yl)-{2-[4-(2-trifluoromethoxybenzenesulfonyl)piperazin-1-yl]ethyl}amine;
(5-Methyl[1,6]naphthyridin-2-yl)-{2-[4-(3-trifluoromethoxybenzenesulfonyl)piperazin-1-yl]ethyl}amine;
(5-Methyl[1,6]naphthyridin-2-yl)-{2-[4-(4-trifluoromethoxybenzenesulfonyl)piperazin-1-yl]ethyl}amine;
{2-[4-(4-Fluorobenzenesulfonyl)piperidin-1-yl]ethyl}-(5-methyl[1,6]naphthyridin-2-yl)amine;
N-{1-[2-(5-Methyl[1,6]naphthyridin-2-ylamino)ethyl]piperidin-4-yl}-C-phenylmethanesulfonamide;
N-{1-[2-(5-Methyl[1,6]naphthyridin-2-ylamino)ethyl]piperidin-4-yl}benzenesulfonamide;
N-{1-[2-(5-Methyl[1,6]naphthyridin-2-ylamino)ethyl]piperidin-4-yl}-4-trifluoromethylbenzenesulfonamide;
{2-[3-(4-Fluorobenzenesulfonyl)piperidin-1-yl]ethyl}-(5-methyl[1,6]naphthyridin-2-yl)amine;
1-[2-(5-Methyl[1,6]naphthyridin-2-ylamino)ethyl]piperidine-4-sulfonic acid benzhydrylamide;
{2-[3-(4-Fluorobenzenesulfonyl)pyrrolidin-1-yl]ethyl}-(5-methyl[1,6]naphthyridin-2-yl)amine;
{2-[4-(2,2-Diphenylethanesulfonyl)piperazin-1-yl]ethyl}-(5-methyl[1,6]naphthyridin-2-yl)amine;
{2-[4-(Diphenylmethanesulfonyl)piperazin-1-yl]ethyl}-(5-methyl[1,6]naphthyridin-2-yl)amine; and
1-{4-[2-(5-Methyl[1,6]naphthyridin-2-ylamino)ethyl]piperazin-1-yl}-3,3-diphenylpropan-1-one,
or a tautomer, or salt thereof.

3. A compound selected from:
[2-(4-Benzylpiperidin-1-yl)ethyl]-(5-methyl[1,6]naphthyridin-2-yl)amine;
(5-Methyl[1,6]naphthyridin-2-yl)-(2-piperidin-1-ylethyl)amine;
1-[2-(5-Methyl[1,6]naphthyridin-2-ylamine)ethyl]piperidin-4-ol;
4-Benzyl-1-[2-(5-methyl[1,6]naphthyridin-2-ylamino)ethyl]piperidin-4-ol;
4-[2-(5-Methyl[1,6]naphthyridin-2-ylamino)ethyl]piperazine-1-carboxylic acid tert-butyl ester;
[2-(4-Benzylpiperazin-1-yl)ethyl]-(5-methyl[1,6]naphthyridin-2-yl)amine;
{2-[4-(4-Chlorophenyl)piperazin-1-yl]ethyl}-(5-methyl-1-[1,6]naphthyridin-2-yl)amine;
[2-(4-Benzenesulfonylpiperazin-1-yl)ethyl]-(5-methyl[1,6]naphthyridin-2-yl)amine;
(5-Methyl[1,6]naphthyridin-2-yl)-{2-[4-(3-phenylpropyl)piperazin-1-yl]ethyl}amine;
(5-Methyl[1,6]naphthyridin-2-yl)-[2-(4-phenethylpiperazin-1-yl)ethyl]amine;
[2-(4-Benzylpiperidin-1-yl)ethyl]-(5,7-dimethyl[1,6]naphthyridin-2-yl)amine;
[2-(4-Benzenesulfonylpiperazin-1-yl)ethyl]-(5,7-dimethyl[1,6]naphthyridin-2-yl)amine;
[2-(4-Benzylpiperidin-1-yl)ethyl]-(5-phenyl[1,6]naphthyridin-2-yl)amine;
N,N-Dimethyl-N'-(5-methyl[1,6]naphthyridin-2-yl)ethane-1,2-diamine;
[2-(4-Benzylpiperidin-1-yl)ethyl]-(5-isopropyl[1,6]naphthyridin-2-yl)amine;
[2-(4-Benzylpiperidin-1-yl)ethyl]-(5-ethyl[1,6]naphthyridin-2-yl)amine;
[2-(4-Benzylpiperidin-1-yl)ethyl]-[1,6]naphthyridin-2-ylamine;
[2-(4-Benzylpiperidin-1-yl)ethyl]-(7-methyl[1,6]naphthyridin-2-yl)amine;
(5-Methyl[1,6]naphthyridin-2-yl)-[2-(4-phenethylpiperidin-1-yl)ethyl]amine;
[2-(4-Benzylpiperidin-1-yl)ethyl]-(5-methoxy-7-methyl[1,6]naphthyridin-2-yl)amine;
[2-(4-Benzyloxypiperidin-1-yl)ethyl]-(5-methyl[1,6]naphthyridin-2-yl)amine;
(1-Ethylpyrrolidin-2-ylmethyl)-(5-methyl[1,6]naphthyridin-2-yl)amine;
(5-Methyl[1,6]naphthyridin-2-yl)-(2-pyrrolidin-1-ylethyl)amine;
(2-Azepan-1-ylethyl)-(5-methyl[1,6]naphthyridin-2-yl)amine;
(1-Benzylpyrrolidin-3-yl)-(5-methyl[1,6]naphthyridin-2-yl)amine;
(3-Azepan-1-ylpropyl)-(5-methyl[1,6]naphthyridin-2-yl)amine;
[3-(4-Benzylpiperidin-1-yl)propyl]-(5-methyl[1,6]naphthyridin-2-yl)amine;
(5-Methyl[1,6]naphthyridin-2-yl)-[3-(2-methylpiperidin-1-yl)propyl]amine;
(5-Methyl[1,6]naphthyridin-2-yl)-(3-piperidin-1-ylpropyl)amine;

2-(4-Benzylpiperidin-1-yl)ethyl]methyl(5-methyl[1,6] naphthyridin-2-yl)amine;
[3-(2,6-Dimethylpiperidin-1-yl)propyl]-(5-methyl[1,6] naphthyridin-2-yl)amine;
{2-[4-(4-Fluorophenoxy)piperidin-1-yl]ethyl}-(5-methyl [1,6]naphthyridin-2-yl)amine;
(5-Methyl[1,6]naphthyridin-2-yl)-{2-[4-(4-trifluoromethylphenoxy)piperidin-1-yl]ethyl}amine;
[2-(1-Benzylpiperidin-4-yl)ethyl]-(5-methyl[1,6]naphthyridin-2-yl)amine;
{1-[2-(5-Methyl[1,6]naphthyridin-2-ylamino)ethyl]piperidin-4-yl}diphenylmethanol;
1-[2-(4-Benzylpiperidin-1-yl)ethyl]-3-(5-methyl[1,6] naphthyridin-2-yl)urea;
[2-(4-Benzhydryloxypiperidin-1-yl)ethyl]-(5-methyl[1,6] naphthyridin-2-yl)amine;
{2-[4-(3,5-Dimethoxybenzyloxy)piperidin-1-yl]ethyl}-(5-methyl[1,6]naphthyridin-2-yl)amine;
(5-Methyl[1,6]naphthyridin-2-yl)-{2-[4-(5-methyl[1,6] naphthyridin-2-yl)piperazin-1-yl]ethyl}amine;
(5-Methyl[1,6]naphthyridin-2-yl)-{2-[4-(3-phenylpropyl) piperidin-1-yl]ethyl}amine;
(5-Methyl[1,6]naphthyridin-2-yl)-{2-[4-(4-trifluoromethylbenzenesulfonyl)piperazin-1-yl]ethyl}amine;
4-{4-[2-(5-Methyl[1,6]naphthyridin-2-ylamino)ethyl] piperazine-1-sulfonyl}benzonitrile;
{2-[4-(4-Fluorobenzenesulfonyl)piperazin-1-yl]ethyl}-(5-methyl[1,6]naphthyridin-2-yl)amine;
{2-[4-(4-Methoxybenzenesulfonyl)piperazin-1-yl]ethyl}-(5-methyl[1,6]naphthyridin-2-yl)amine;
{2-[4-(6-Chloropyridine-3-sulfonyl)piperazin-1-yl] ethyl}-(5-methyl[1,6]naphthyridin-2-yl)amine;
[2-(4-Methanesulfonylpiperazin-1-yl)ethyl]-(5-methyl[1, 6]naphthyridin-2-yl)amine;
(5-Methyl[1,6]naphthyridin-2-yl)-[2-(4-phenylmethanesulfonylpiperazin-1-yl)ethyl]amine;
{2-[4-(4-Bromobenzenesulfonyl)piperazin-1-yl]ethyl}-(5-methyl[1,6]naphthyridin-2-yl)amine;
{2-[4-(4-Chlorobenzenesulfonyl)piperazin-1-yl]ethyl}-(5-methyl[1,6]naphthyridin-2-yl)amine;
{2-[4-(4-Methanesulfonylbenzenesulfonyl)piperazin-1-yl]ethyl}-(5-methyl[1,6]naphthyridin-2-yl)amine;
{2-[4-(4-tert-Butylbenzenesulfonyl)piperazin-1-yl] ethyl}-(5-methyl[1,6]naphthyridin-2-yl)amine;
(5-Methyl[1,6]naphthyridin-2-yl)-{2-[4-(2,4,6-trichlorobenzenesulfonyl)piperazin-1-yl]ethyl}amine;
(5-Methyl[1,6]naphthyridin-2-yl)-{2-[4-(2-trifluoromethoxybenzenesulfonyl)piperazin-1-yl] ethyl}amine;
(5-Methyl[1,6]naphthyridin-2-yl)-{2-[4-(3-trifluoromethoxybenzenesulfonyl)piperazin-1-yl] ethyl}amine;
(5-Methyl[1,6]naphthyridin-2-yl)-{2-[4-(4-trifluoromethoxybenzenesulfonyl)piperazin-1-yl] ethyl}amine;
{2-[4-(4-Fluorobenzenesulfonyl)piperidin-1-yl]ethyl}-(5-methyl[1,6]naphthyridin-2-yl)amine;
N-{1-[2-(5-Methyl[1,6]naphthyridin-2-ylamino)ethyl]piperidin-4-yl}-C-phenylmethanesulfonamide;
N-{1-[2-(5-Methyl[1,6]naphthyridin-2-ylamino)ethyl]piperidin-4-yl}-benzenesulfonamide;
N-{1-[2-(5-Methyl[1,6]naphthyridin-2-ylamino)ethyl]piperidin-4-yl}-4-trifluoromethylbenzenesulfonamide;
{2-[3-(4-Fluorobenzenesulfonyl)piperidin-1-yl]ethyl}-(5-methyl[1,6]naphthyridin-2-yl)amine;
1-[2-(5-Methyl[1,6]naphthyridin-2-ylamino)ethyl]piperidine-4-sulfonic acid benzhydrylamide;
{2-[3-(4-Fluorobenzenesulfonyl)pyrrolidin-1-yl]ethyl}-(5-methyl[1,6]naphthyridin-2-yl)amine;
{2-[4-(2,2-Diphenylethanesulfonyl)piperazin-1-yl] ethyl}-(5-methyl[1,6]naphthyridin-2-yl)amine;
{2-[4-(Diphenylmethanesulfonyl)piperazin-1-yl]ethyl}-(5-methyl[1,6]naphthyridin-2-yl)amine; and
1-{4-[2-(5-Methyl[1,6]naphthyridin-2-ylamino)ethyl] piperazin-1-yl}-3,3-diphenylpropan-1-one,
or a tautomer, or salt thereof.

* * * * *